(12) United States Patent
Rodriguez-Borlado et al.

(10) Patent No.: US 11,529,376 B2
(45) Date of Patent: Dec. 20, 2022

(54) METHODS OF TREATING SYSTEMIC GRAFT-VERSUS-HOST DISEASE WITH EXTRACELLULAR VESICLES

(71) Applicant: Capricor, Inc., Beverly Hills, CA (US)

(72) Inventors: Luis Rodriguez-Borlado, Redondo Beach, CA (US); Houman Hemmati, Santa Monica, CA (US); Kiel A. Peck, West Hollywood, CA (US); Linda Marban, Santa Monica, CA (US); Jennifer J. Moseley, Northborough, MA (US)

( * ) Notice: Subject to any disclaimer, the term of this patent is extended or adjusted under 35 U.S.C. 154(b) by 153 days.

(21) Appl. No.: 16/610,859

(22) PCT Filed: May 4, 2018

(86) PCT No.: PCT/US2018/031257
§ 371 (c)(1),
(2) Date: Nov. 4, 2019

(87) PCT Pub. No.: WO2018/204889
PCT Pub. Date: Nov. 8, 2018

(65) Prior Publication Data
US 2020/0054686 A1    Feb. 20, 2020

Related U.S. Application Data

(60) Provisional application No. 62/502,474, filed on May 5, 2017, provisional application No. 62/506,880, filed on May 16, 2017.

(51) Int. Cl.
| A61K 35/14 | (2015.01) |
| A61K 35/00 | (2006.01) |
| A61K 35/50 | (2015.01) |
| A61P 37/06 | (2006.01) |
| A61K 9/00 | (2006.01) |
| A61K 35/28 | (2015.01) |
| A61K 35/34 | (2015.01) |
| A61K 35/51 | (2015.01) |
| A61K 35/545 | (2015.01) |

(52) U.S. Cl.
CPC ............ *A61K 35/50* (2013.01); *A61K 9/0019* (2013.01); *A61K 35/28* (2013.01); *A61K 35/34* (2013.01); *A61K 35/51* (2013.01); *A61K 35/545* (2013.01); *A61P 37/06* (2018.01)

(58) Field of Classification Search
None
See application file for complete search history.

(56) References Cited

FOREIGN PATENT DOCUMENTS

WO    WO2016043654 A1 *  3/2016

OTHER PUBLICATIONS

Henriques (the Y reference) of (the article titled Capicor Awarded $2.4 million by U.S. DoD to Develop Therapeutic Exosome. Press release [on line] Sep. 28, 2016). (Year: 2016).*
Wang et al. ("Extracellular Vesicles Released from Human Umbilical Cord-Derived Mesenchymal Stromal Cells Prevent Life-Threatening Acute Graft-Versus-Host Disease in a Mouse Model of Allogeneic Hematopoietic etc.", Stem Cells and Development, vol. 25, No. 24, 2016, pp. 1874-1883) (Year: 2016).*

* cited by examiner

*Primary Examiner* — Michael Barker
*Assistant Examiner* — Randall O Winston
(74) *Attorney, Agent, or Firm* — Capricor, Inc.; Joseph E. Zahner

(57) ABSTRACT

The present invention relates to a method of treating acute or chronic systemic graft-versus-host disease (GVHD) with extracellular vesicles, e.g., exosomes obtained from human cardiospheres or cardiosphere-derived cells (CDCs), wherein systemic GVHD involves, e.g., at least two organs selected from the group consisting of the skin, mucosa, gastrointestinal tract, liver, lungs, joints and fascia, genitalia, and eyes. The present invention also provides a pharmaceutical formulation comprising extracellular vesicles, e.g., exosomes obtained from human cardiospheres or CDCs, for systemic administration, e.g., intravenous infusion, to a human subject in need of treatment of systemic GVHD.

18 Claims, 22 Drawing Sheets

Experimental design

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

Data is presented as mean ± SEM.

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

Data is presented as mean ± SEM.

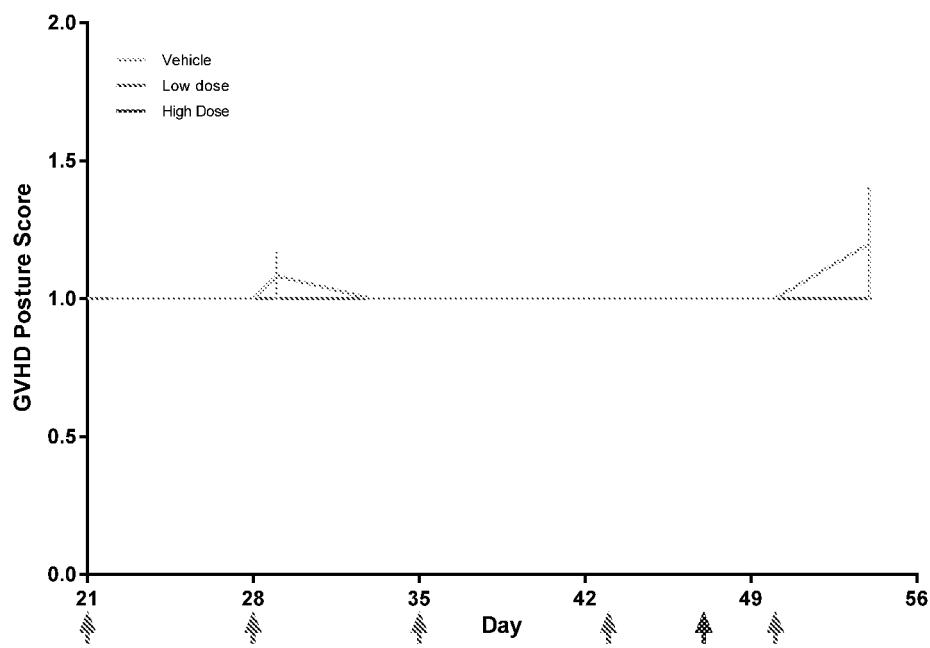

Fig. 8A

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

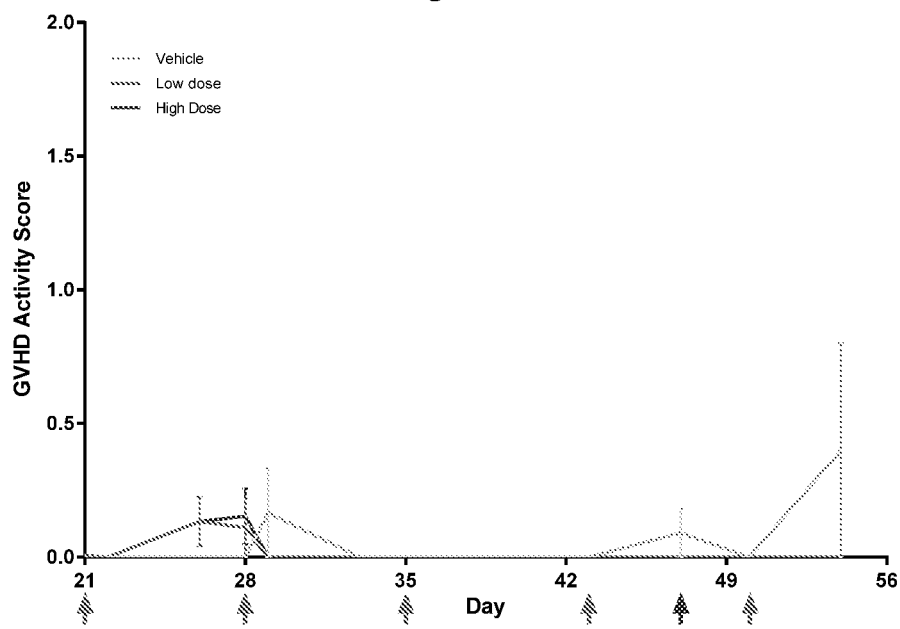

Fig. 8B

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

Fig. 8C

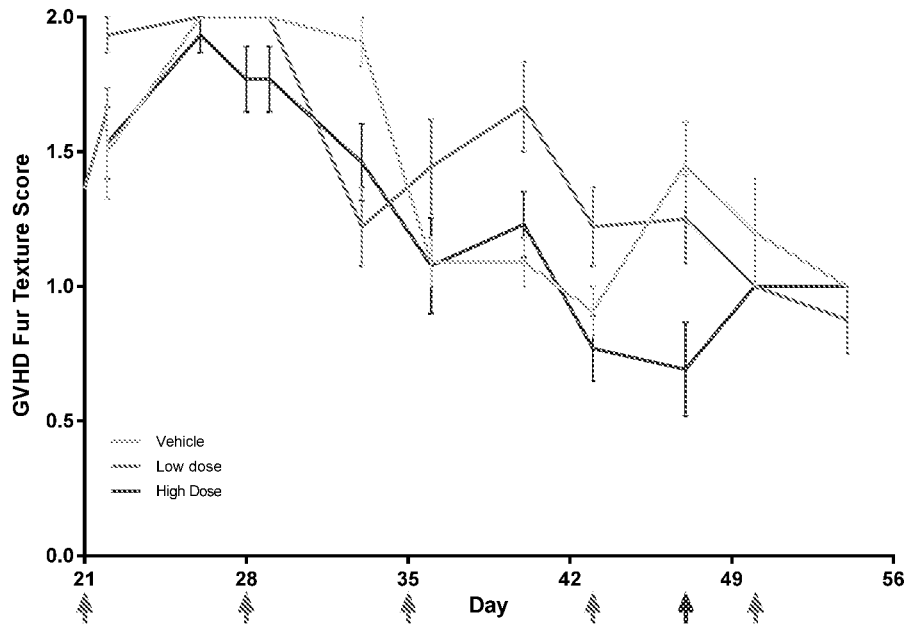

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

Fig. 8D

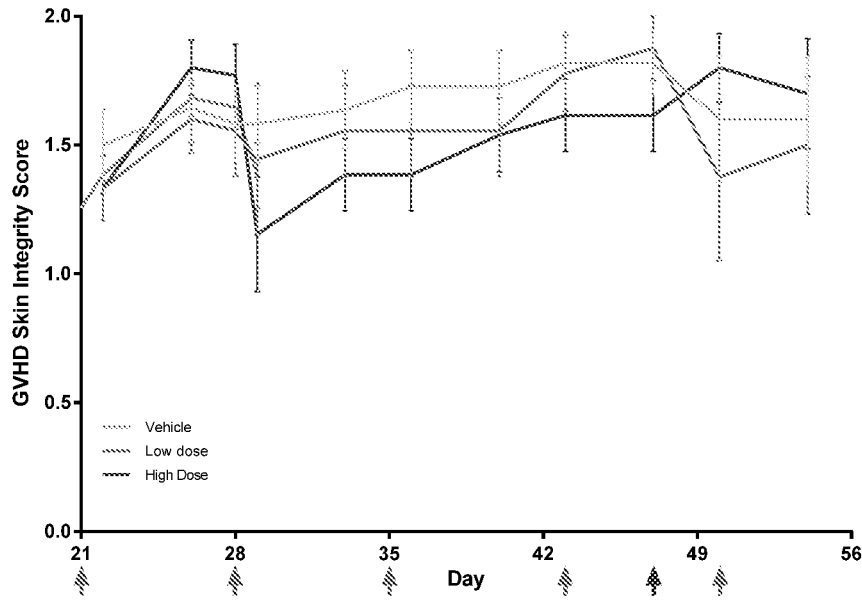

Data is presented as mean ± SEM. Red arrows = dosing days for all groups. Blue arrow at Day 47 for Group 3 only. Dosage for Group 3 was switched to 2x/week from Day 43 to study end, as described in Tables 2 and 3.

Red arrows = dosing days for all groups. Blue arrow at Day 47 for Group 3 only. Dosage for Group 3 was switched to 2x/week from Day 43 to study end, as described in Tables 2 and 3.

Diarrhea Incidence: Diarrhea incidence was tracked during the study. Data represent mean ± SEM. Data is presented as mean ± SEM.

Diarrhea Incidence: Data represent individual data points with black horizontal lines represent mean ± SEM.

Eye inflammation was evaluated independently in each eye. Data is presented as mean ± SEM.

Eye inflammation was assayed. Data is presented as mean ± SEM.

Eye inflammation: Individual data points with black horizontal lines represent mean ± SEM.

Mouse Colon Colitis Scores. Group mean +/- standard error of the mean (SEM); scores were assigned according to the colitis scoring scheme showed in Tables 5-8.

Mouse Colon Sum Colitis Scores. Group mean +/- SEM. Sum score was slightly lower in low dose test article-treated (Group 2) mice compared to untreated (Group 1).

Mouse Colon Histopathology Severity Scores. Group mean +/- SEM. Group 2 had less severe erosions and more hyperplasia compared to Group 1.

Mouse Eye Histopathology Severity Scores. Group mean +/- SEM. Corneal lymphocytic satellitosis, corneal and uveal inflammation and neovascularization were most severe in untreated mice (Group 1).

Results are mean percentage values ± SEM from 3 different donors each done in triplicates.

Results are mean percentage values ± SD obtained from triplicates.

Results are mean values ± SD obtained from triplicates.

Results are mean percentage values ± SEM from 2 different donors each done in triplicates.

METHODS OF TREATING SYSTEMIC GRAFT-VERSUS-HOST DISEASE WITH EXTRACELLULAR VESICLES

BACKGROUND OF THE INVENTION

Graft-versus-host disease (GVHD) occurs when cells transplanted from a non-identical donor (typically bone marrow, T-cell, and/or hematopoietic stem cell donor; the graft) recognize and mount a deleterious immune response against antigens found in the transplant recipient (the host). See, e.g., Billingham, "The Biology of Graft-Versus-Host Reactions," Harvey Lect., 62:21-78 (1966-1967). The disease presents as a heterogeneous condition involving multiple organs, most commonly the skin, mucosa, gastrointestinal tract, liver and lungs. For patients undergoing allogeneic hematopoietic stem cell transplant (HSCT), GVHD is a significant cause of morbidity and mortality. Due to the large number of variables affecting disease risk, there is a wide range of incidence reported for both acute and chronic GVHD. Up to 80% of patients will develop GVHD at approximately 14-21 days following HSCT (acute), and of those surviving beyond 100 days, between 30 and 70% will develop chronic GVHD. Unsurprisingly, chronic GVHD represents the single leading cause of death in HSCT survivors. See, e.g., Pasquini et al., "2010 Report from the Center for International Blood and Marrow Transplant Research (CIBMTR): Current Uses and Outcomes of Hematopoietic Cell Transplants for Blood and Bone Marrow Disorders," Clin Transpl., 87-105 (2010).

Development of GVHD is dependent on the activation of antigen-specific donor T cells that are able to mount a specific immune response targeting host tissues. This event is potentiated by conditioning of the host prior to HSCT in order to suppress the immune system and ensure effective engraftment. Host tissue damage is mediated by cytotoxic T cells involving a variety of mechanisms, including direct cell contact and the production of soluble pro-inflammatory mediators. See, e.g., Ferrara et al., "Graft-Versus-Host Disease," Lancet, 373:1550-1561 (2009); Sakoda et al., "Donor-Derived Thymic-Dependent T Cells Cause Chronic Graft-Versus-Host Disease," Blood, 109:1756-1764 (2010). Multiple T-helper cell subsets have been shown to be involved, including Th1, Th2, and Th17. See, e.g., Broady et al., "Cutaneous GVHD is Associated with the Expansion of Tissue-Localized Th1 and not Th17 Cells," Blood, 116: 5749-5751 (2010); Murphy et al., "Differential Effects of the Absence of Interferon-Gamma and IL-4 in Acute Graft-Versus-Host Disease After Allogeneic Bone Marrow Transplantation in Mice," J Clin Invest., 102:1742-1748 (1998); Nikolic et al., "Th1 and Th2 Mediate Acute Graft-Versus-Host Disease, each with Distinct End-Organ Targets," J Clin Invest., 105:1289-1298 (2000). The current understanding of their specific roles is complex: in some models, Th17 cells have been shown to be sufficient for induction of GVHD, whereas in others their absence has been shown to exacerbate disease. See, e.g., Yi et al., "Absence of Donor Th17 Leads to Augmented Th1 Differentiation and Exacerbated Acute-Graft-Versus-Host Disease," Blood, 112:2101-2110 (2008); Kappel et al., "IL-17 Contributes to CD4-Mediated Graft-Versus-Host Disease," Blood, 113:945-952 (2009).

Despite the advances in understanding the immunopathological basis of the disease and associated risk factors, and the development of more effective MHC matching and immune conditioning, little progress has been made in decreasing late transplantation-related mortality. The focus of current therapy is general immune suppression using corticosteroids, which has dubious efficacy; sustained amelioration of disease symptoms are only seen in around 50% of patients. See, e.g., Billingham, "The Biology of Graft-Versus-Host Reactions," Harvey Lect., 62:21-78 (1966-1967). More promising therapies are based on the prophylactic prevention of GVHD, and use T cell targeting agents such as methotrexate and tacrolimus. This lack of success is mainly the result of the failure to reduce the incidence and severity of chronic GVHD.

Cells release into the extracellular environment diverse types of membrane vesicles of endosomal and plasma membrane origin called exosomes and microvesicles, respectively. These extracellular vesicles represent an important mode of intercellular communication by serving as vehicles for transfer between cells of membrane and cytosolic proteins, lipids, and RNA. See, e.g., Graga Raposo and Willem Stoorvogel, "Extracellular Vesicles: Exosomes, Microvesicles, and Friends," The Journal of Cell Biology, Vol. 200, No. 4, 373-383 (2013). WO 2014/028493 describes exosomes derived from cardiosphere-derived cells (CDCs) and their therapeutic utility for the repair or regeneration of damaged or diseased cells or tissue, e.g., damaged cardiac tissue. US 2012/0315252 describes CDCs, their derivation from cardiospheres, and their therapeutic utility for increasing the function of a damaged or diseased heart of a mammal. WO 2005/012510 describes cardiospheres, their derivation from human or animal cardiac tissue biopsy samples, and their therapeutic utility in cell transplantation and functional repair of the myocardium or other organs.

SUMMARY OF THE INVENTION

The present invention is based on the surprising discovery by the present inventors that extracellular vesicles, in particular exosomes derived from cardiosphere-derived cells (CDCs), have immunomodulatory capabilities on T cells and are effective in treating systemic graft-versus-host disease (GVHD), as demonstrated for the first time in a relevant mouse model of systemic GVHD. The advantage of the method of the present invention as described herein is that it is a safe, systemically-administered biologic therapy that can improve both survival and end-organ damage (e.g., gastrointestinal tract and eyes) in GVHD by modulating the immune response and reducing inflammation and fibrosis. This causes reduction in end-organ morbidities such as ocular GVHD and weight loss attributable to poor nutrient absorption in the gastrointestinal tract, leading to inter alia improved survival and presumably enhanced quality of life.

For the purpose of the present invention, the term "systemic GVHD" is used interchangeably with "GVHD", and refers to acute or chronic GVHD requiring or amenable to treatment by systemic administration of extracellular vesicles, e.g. exosomes and/or microvesicles, derived from CDCs.

Generally, the present invention provides a method of safely treating systemic GVHD in a subject in need thereof, the method comprising systemically administrating to the subject a therapeutically effective amount of extracellular vesicles, e.g., exosomes and/or microvesicles, derived from CDCs, wherein systemic GVHD is a syndrome involving multiple organs, most commonly the skin, mucosa, gastrointestinal tract, liver, and lungs, wherein cells originating from a donor (typically bone marrow, T-cell, and/or hematopoietic stem cell donor) recognize and mount a deleterious immune response against antigens found in the immunocompromised recipient.

According to one aspect of the present invention, systemic administration of a therapeutically effective amount of extracellular vesicles, e.g., exosomes and/or microvesicles, derived from CDCs, results in treatment of systemic GVHD with respect to at least one organ selected from the group consisting of the skin, mucosa, gastrointestinal tract, liver, and lungs. Alternatively, according to the present invention, said administration of a therapeutically effective amount of extracellular vesicles results in treatment of systemic GVHD with respect to at least two organs selected from the group consisting of the skin, mucosa, gastrointestinal tract, liver, and lungs.

According to another aspect of the present invention, systemic administration of a therapeutically effective amount of extracellular vesicles, e.g., exosomes and/or microvesicles, derived from CDCs, results in treatment of systemic GVHD with respect to at least one organ selected from the group consisting of the skin, mucosa, gastrointestinal tract, liver, lungs, joints and fascia, and genitalia. Alternatively, according to the present invention, said administration of a therapeutically effective amount of extracellular vesicles results in treatment of systemic GVHD with respect to at least two organs selected from the group consisting of the skin, mucosa, gastrointestinal tract, liver, lungs, joints and fascia, and genitalia.

According to another aspect of the present invention, systemic administration of a therapeutically effective amount of extracellular vesicles, e.g., exosomes and/or microvesicles, derived from CDCs, results in treatment of systemic GVHD with respect to at least one organ selected from the group consisting of the skin, mucosa, gastrointestinal tract, liver, lungs, joints and fascia, and genitalia, and the eyes.

According to another aspect of the present invention, systemic administration of a therapeutically effective amount of extracellular vesicles, e.g., exosomes and/or microvesicles, derived from CDCs, results in treatment of systemic GVHD with respect to the eyes.

According to the present invention, a therapeutically effective amount of extracellular vesicles, e.g., exosomes and/or microvesicles, derived from CDCs, is systemically administered one or more times after the subject has undergone HSCT. In some embodiments, a therapeutically effective amount of extracellular vesicles is systemically administered to the subject less than, e.g., 1 hour post HSCT. In some embodiments, a therapeutically effective amount of extracellular vesicles is systemically administered to the subject less than, e.g., 1-24 hours post HSCT. In some embodiments, a therapeutically effective amount of extracellular vesicles is systemically administered to the subject less than, e.g., 24-48 hours post HSCT. In some embodiments, a therapeutically effective amount of extracellular vesicles is systemically administered to the subject, e.g., 1-2 weeks post HSCT. In some embodiments, a therapeutically effective amount of extracellular vesicles is systemically administered to the subject, e.g., 2-3 weeks after post HSCT. In some embodiments, a therapeutically effective amount of extracellular vesicles is systemically administered to the subject, e.g., 4-8 weeks post HSCT. In some embodiments, a therapeutically effective amount of extracellular vesicles is systemically administered to the subject, e.g., 1, 2, 3, 4, 5, 6, 7, and/or 8 weeks after HSCT, one or more times, e.g., 7 days apart between successive administrations.

According to the present invention, said subject is a mammal, e.g., a human; said systemic administration is via, e.g., intra-vascular administration, intraventricular administration, intrathecal administration, or intraperitoneal administration, wherein said intra-vascular administration is, e.g., intravenous, intra-arterial, or intracoronary infusion or injection; According to the present invention, said extracellular vesicles are exosomes, microvesicles, membrane particles, membrane vesicles, exosome-like vesicles, ectosomes, ectosome-like vesicles, exovesicles, epididimosomes, argosomes, promininosomes, prostasomes, dexosomes, texosomes, archeosomes, oncosomes, or the like.

According to an embodiment of the present invention, said extracellular vesicles are derived from CDCs cultured in serum-free medium (e.g., IMDM) and incubated at about 5% $O_2$ for about 15 days, wherein said extracellular vesicles are obtained after filtering CDC condition medium containing extracellular vesicles through a 1000 kDa pore sized filter. More generally, according to the present invention, said extracellular vesicles are derived from CDCs cultured in serum-containing or serum-free medium and incubated at 2-20% $O_2$ for 1-15 days, wherein said extracellular vesicles are obtained after filtering CDC condition medium containing extracellular vesicles through a 3-1000 kDa (e.g., 10 kDa) pore sized filter. Alternatively, extracellular vesicles are obtained by precipitation with polyethylene glycol (e.g., 25% PEG).

According to the present invention, extracellular vesicles, e.g., exosomes, are formulated in a crystalloid solution (e.g., Plasmalyte, normal saline), aqueous solution, gel, ointment, cream, topical or implantable hydrogel, powder, sustained-release polymer (e.g., PLGA and PLA), polyethylene glycol (PEG)-containing solution, suspension, emulsion, as part of a drug delivery device, insert, patch, or the like. In several embodiments, prior to use, extracellular vesicles, e.g., exosomes, are resuspended in an appropriate buffer, e.g., sterile PBS with or without human serum albumin. In some embodiments, exosomes can be stored for future use, e.g., frozen at −80° C.

In several embodiments, extracellular vesicles, e.g., exosomes, are derived from human or animal cells. In several embodiments, extracellular vesicles, e.g., exosomes, are prepared from cardiospheres or CDCs. In some embodiments, extracellular vesicles, e.g., exosomes, are prepared from regenerative stem cells such as embryonic stem cells, pluripotent stem cells, multipotent stem cells, induced pluripotent stem cells, post-natal stem cells, adult stem cells, mesenchymal stem cells, hematopoietic stem cells, endothelial stem cells, epithelial stem cells, neural stem cells, cardiac stem cells including cardiac progenitor cells, bone marrow-derived stem cells, adipose-derived stem cells, hepatic stem cells, peripheral blood derived stem cells, cord blood-derived stem cells, placental stem cells, or the like.

In several embodiments, extracellular vesicles, e.g., exosomes, are modified (e.g., genetically or otherwise) to direct them to a specific target site. For example, a modification may, in some embodiments, comprise inducing expression of a specific cell-surface marker on the exosome, which results in specific interaction with a receptor on a desired target tissue. In one embodiment, the native contents of the exosome are removed and replaced with, or supplemented with, desired exogenous proteins and/or nucleic acids.

In several embodiments, extracellular vesicles, e.g., exosomes, include one or more microRNAs selected from: miR-146a, miR-148a, miR-22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a. In a preferred embodiment, extracellular vesicles, e.g., exosomes, comprise miR-146a and miR-210. In several embodiments, extracellular vesicles, e.g., exosomes, include one or more microRNAs selected from: hsa-miR-23a-3p, hsa-miR-130a-3p, hsa-miR-21-5p, hsa-miR-4516, hsa-let-7a-5p, hsa-miR-125b-5p, hsa-miR-199a-3p, hsa-miR-199b-3p, hsa-miR-22-3p, hsa-miR-24-3p, hsa-miR-1290, hsa-miR-320e, hsa-miR-423-5p, hsa-miR-22-3p, hsa-miR-222-3p (also known as miR-221-3p), hsa-miR-100-5p, hsa-miR-337-5p, hsa-miR-27b-3p, hsa-miR-1915-3p, and hsa-miR-29b-3p, hsa-miR-25-3p (also known as miR-92a-3p).

In several embodiments, extracellular vesicles, e.g., exosomes, contain biological proteins, e.g., transcription factors, cytokines, growth factors, and similar proteins capable of modulating signaling pathways in a target cell. In some embodiments, the biological protein is capable of facilitating regeneration and/or improved function of a tissue. In some embodiments, the biological protein is capable of modulating pathways related to Irak1, Traf6, toll-like receptor (TLR) signaling pathway, NOX-4, SMAD-4, and/or TGF-β. In some embodiments, the biological protein is related to exosome formation and packaging of cytosolic proteins such as Hsp70, Hsp90, 14-3-3 epsilon, PKM2, GW182 and AGO2. In some embodiments, extracellular vesicles, e.g., exosomes, contain signaling lipids, e.g., ceramide and derivatives.

In several embodiments, extracellular vesicles, e.g., exosomes, express tetraspanins, e.g., CD63, CD81, CD82, CD53, and/or CD37. In some embodiments, extracellular vesicles, e.g., exosomes, express one or more lipid raft associated proteins (e.g., glycosylphosphatidylinositol-anchored proteins and flotillin), cholesterol, sphingomyelin, and/or hexosylceramides.

In several embodiments, extracellular vesicles, e.g., exosomes, have a diameter of, e.g., about 15-250 nm, about 15-205 nm, about 90-220 nm, about 30-200 nm, about 20-150 nm, about 70-150 nm, or about 40-100 nm. In several embodiments, extracellular vesicles, e.g., microvesicles, have a diameter of, e.g., about 100-1000 nm.

In several embodiments, extracellular vesicles, e.g., exosomes, are purified such that contaminants or undesired compounds are removed from the exosomes. In some embodiments, the patient is administered substantially purified exosomes such that about 50% to 90%, or up to 100%, of the contaminants are removed from the exosomes. In some embodiments, an exosome preparation is essentially free of non-exosome components.

In several embodiments, extracellular vesicles, e.g., exosomes, are administered in combination with one or more additional agents. For example, in several embodiments, the exosomes are administered in combination with one or more proteins or nucleic acids derived from the exosome. In several embodiments, the cells from which the exosomes are isolated are administered in conjunction with the exosomes. In several embodiments, such an approach advantageously provides an acute and more prolonged duration of exosome delivery (e.g., acute based on the actual exosome delivery and prolonged based on the cellular delivery, the cells continuing to secrete exosomes post-delivery).

In several embodiments, the dose of extracellular vesicles, e.g., exosomes ranges about $1.0 \times 10^5$ to about $1.0 \times 10^{10}$ exosomes. In certain embodiments, the exosome dose is administered on a per kilogram basis, e.g., about $1.0 \times 10^5$ exosomes/kg to about $1.0 \times 10^9$ exosomes/kg. In additional embodiments, exosomes are delivered in an amount based on the mass of the target tissue, e.g., about $1.0 \times 10^5$ exosomes/gram of target tissue to about $1.0 \times 10^9$ exosomes/gram of target tissue. In several embodiments, exosomes are administered based on a ratio of the number of exosomes to the number of cells in a particular target tissue. If exosomes are to be administered in conjunction with the concurrent therapy (e.g., cells that can still shed exosomes, pharmaceutical therapy, nucleic acid therapy, and the like) the dose of exosomes administered can be adjusted accordingly (e.g., increased or decreased as needed to achieve the desired therapeutic effect).

The present invention further provides a formulation comprising extracellular vesicles for use in the treatment of systemic GVHD according to the aforementioned method.

The present invention further provides a use of the aforementioned formulation for treating systemic GVHD according to the aforementioned method.

BRIEF DESCRIPTION OF THE DRAWINGS

FIG. 8A graphically shows the effects of intravenous administration of extracellular vesicles on the posture criterion of the GVHD score.

FIG. 8B graphically shows the effects of intravenous administration of extracellular vesicles on the activity criterion of the GVHD score.

FIG. 8C graphically shows the effects of intravenous administration of extracellular vesicles on the fur activity criterion of the GVHD score.

FIG. 8D graphically shows the effects of intravenous administration of extracellular vesicles on the skin integrity criterion of the GVHD score.

DETAILED DESCRIPTION OF THE INVENTION

A) Clinical Manifestations

Figure 1:
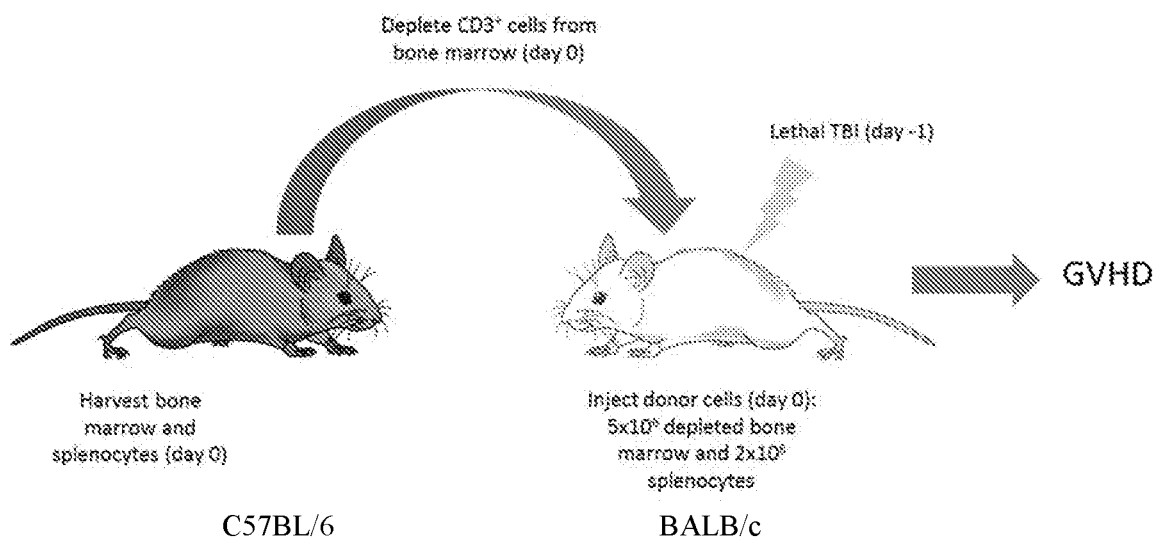
FIG. 1 is a diagram showing how systemic GVHD is induced in BALB/c mice.

GVHD has been classically divided into acute and chronic variants based upon the time of onset using a cutoff of 100 days. Clinical manifestations of chronic GVHD include skin involvement resembling lichen planus or the cutaneous manifestations of scleroderma, dry oral mucosa with ulcerations and sclerosis of the gastrointestinal tract, and a rising serum bilirubin concentration. In contrast, patients with acute GVHD commonly demonstrate a classic maculopapular rash, abdominal cramps with diarrhea, and a rising serum bilirubin concentration. However, this conventional division has been challenged by the recognition that signs of acute and chronic GVHD may occur outside of these designated periods. This observation has led to the increased use of clinical findings, rather than a set time period, to differentiate between acute and chronic GVHD. The widely accepted National Institutes of Health (NIH) consensus criteria for the diagnosis of GVHD include an overlap syndrome in which diagnostic or distinctive features of chronic GVHD and acute GVHD appear together. See, e.g., Filipovich et al., "National Institutes of Health Consensus Development Project on Criteria for Clinical Trials in Chronic Graft-Versus-Host Disease: I. Diagnosis and Staging Working Group Report," *Biol Blood Marrow Transplant*, 11(12):945 (2005).

The NIH consensus criteria for identifying signs and symptoms of chronic GVHD are summarized in Table 1. See, e.g., Jagasia et al., "National Institutes of Health Consensus Development Project on Criteria for Clinical Trials in Chronic Graft-versus-Host Disease: I. The 2014 Diagnosis and Staging Working Group Report," *Biol Blood Marrow Transplant*, 21:389 (2015).

TABLE 1

| Organ | Score 1 | Score 2 | Score 3 |
| --- | --- | --- | --- |
| Skin: GVHD features to be scored by body surface area (BSA): maculopapular rash/erythema; lichen planus-like features; sclerotic features; papulosquamous lesions or ichthyosis; keratosis pilaris-like GVHD | 1-18% BSA involved | 19-50% BSA involved; superficial sclerotic features "not hidebound" (able to pinch) | >50% BSA involved; deep sclerotic features; "hidebound" (unable to pinch); impaired mobility; ulceration |
| Mouth: Lichen planus-like features | Mild symptoms with disease signs but not limiting oral intake significantly | Moderate symptoms with disease signs with partial limitation of oral intake | Severe symptoms with disease signs on examination with major limitation of oral intake |
| Gastrointestinal Tract: Esophageal web/proximal stricture or ring; dysphagia; anorexia; nausea; vomiting; diarrhea; weight loss; failure to thrive | Symptoms without significant weight loss (<5%) | Symptoms associated with mild to moderate weight loss (5-15%), or moderate diarrhea without significant interference with daily living | Symptoms associated with significant weight loss (>15%); requires nutritional supplement for most calorie needs, or esophageal dilation, or severe diarrhea with significant interference with daily living |
| Liver | | Normal total bilirubin with alanine aminotransferase (ALT) ≥3-5 x upper limit of normal (ULN), or alkaline phosphatase (AP) ≥3 x ULN | Elevated total bilirubin but ≤3 mg/dL, or ALT >5 ULN | Elevated total bilirubin but >3 mg/dL |

TABLE 1-continued

| Organ | Score 1 | Score 2 | Score 3 |
|---|---|---|---|
| Lungs:<br>Pulmonary function tests | Mild symptoms (shortness of breath after climbing one flight of steps); forced expiratory volume in 1 second (FEV1) ≥60-79% | Moderate symptoms (shortness of breath after walking on flat ground); FEV1 = 40-59% | Severe symptoms (shortness of breath at rest; requiring $O_2$); FEV1 ≤ 39% |
| Joints and Fascia | Mild tightness of arms or legs, normal or mild decreased range of motion (ROM), and not affecting ADL | Tightness of arms or legs, or joint contractures, erythema thought due to fasciitis, decreased ROM, and mild to moderate limitation of ADL | Contractures with significant decrease of ROM, and significant limitation of ADL (unable to tie shoes, button shirts, dress self, etc.) |
| Genital Tract | Mild signs and females with or without discomfort on exam | Moderate signs and may have symptoms with discomfort on exam | Severe signs with or without symptoms |
| Eyes:<br>Keratoconjunctivitis sicca (KCS) confirmed by ophthalmologist | Mild dry eye symptoms not affecting activities of daily living (ADL); requiring lubricant eye drops ≤3 x per day | Moderate dry eye symptoms partially affecting ADL; requiring lubricant eye drops >3 x per day or punctal plugs; without new vision impairment due to KCS | Severe dry eye symptoms significantly affecting ADL; Special eyeware to relieve pain, or unable to work because of ocular symptoms, or loss of vision due to KCS |

Patients diagnosed with chronic GVHD are then subclassified based upon the presence or absence of features of acute GVHD into one of two categories:

Classic chronic GVHD: Features of chronic GVHD are present without signs or symptoms of acute GVHD.

Overlap syndrome: Features of both chronic GVHD and acute GVHD are present.

Features of acute GVHD seen in the overlap syndrome include changes in the skin (skin erythema, maculopapular rash, pruritus), mouth (gingivitis, mucositis, oral erythema, oral pain), gastrointestinal symptoms (anorexia, nausea, vomiting, diarrhea, weight loss, failure to thrive), liver dysfunction (elevations in bilirubin, alkaline phosphatase, ALT, or AST), and organizing pneumonia (also called bronchiolitis obliterans organizing pneumonia).

For the purpose of the present invention, terms such as "treating" and "treatment" as used herein refer to therapeutic measures that cure, slow down, lessen symptoms of, and/or halt progression of a diagnosed pathologic condition or disorder. For instance, a subject is successfully "treated" according to the methods of the present invention if the subject shows clinical improvement according to the NIH consensus criteria for identifying signs and symptoms of chronic GVHD.

B) Cardiospheres

Cardiospheres are undifferentiated cardiac cells that grow as self-adherent clusters as described in WO 2005/012510, and Messina et al., "Isolation and Expansion of Adult Cardiac Stem Cells From Human and Murine Heart," *Circulation Research*, 95:911-921 (2004), the disclosures of which are herein incorporated by reference in their entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal or ventricle wall, atrial appendages, or combinations thereof. A biopsy can be obtained, e.g., by using a percutaneous bioptome as described in, e.g., U.S. Patent Application Publication Nos. 2009/012422 and 2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like. The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium comprising buffered media, amino acids, nutrients, serum or serum replacement, growth factors including but not limited to EGF and bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated.

C) Cardiosphere-Derived Cells (CDCs)

CDCs are a population of cells generated by manipulating cardiospheres in the manner as described in, e.g., U.S. Patent Application Publication No. 2012/0315252, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods.

D) Exosomes

Exosomes are vesicles formed via a specific intracellular pathway involving multivesicular bodies or endosomal-related regions of the plasma membrane of a cell. Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, as described in WO 2014/028493, miR146a exhibits over a 250-fold increased expression in CDCs, and miR210 is upregulated approximately 30-fold, as compared to the exosomes isolated from normal human dermal fibroblasts.

Exosomes derived from cardiospheres and CDCs are described in, e.g., WO 2014/028493, the disclosures of which are herein incorporated by reference in their entirety. Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and U.S. Application Publication Nos. 2012/0093885 and 2014/0004601. Methods for isolating exosome from cardiosphere-derived cells are found in, e.g., Ibrahim et al., Stem Cell Reports, 2:606-619 (2014). Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cutoff (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

E) Examples

The present invention is further described with reference to the following non-limiting examples.

Example 1: CDC Culture

CDCs were prepared as described in U.S. Patent Application Publication No. 2012/0315252, the disclosures of which are herein incorporated by reference in their entirety.

In brief, heart biopsies were minced into small fragments and briefly digested with collagenase. Explants were then cultured on 20 mg/mL fibronectin-coated dishes. Stromal-like flat cells and phase-bright round cells grew out spontaneously from tissue fragments and reached confluency by 2-3 weeks. These cells were harvested using 0.25% trypsin and were cultured in suspension on 20 mg/mL poly-d-lysine to form self-aggregating cardiospheres. CDCs were obtained by plating and expanding the cardiospheres on a fibronectin-coated flask as an adherent monolayer culture. All cultures were maintained at 5% 02, 5% $CO_2$ at 37° C., using IMDM basic medium supplemented with 10% FBS, 1% penicillin/streptomycin, and 0.1 mL 2-mercaptoethanol. CDCs were grown to 100% confluency on a fibronectin-coated flask to passage 5.

Example 2: Isolation of Exosomes from CDCs

When the CDCs reached the desired confluency, the flask was washed three times with PBS. CDCs were treated with serum-free medium (IMDM) and were incubated at 37° C. at 5% 02, 5% $CO_2$ for 15 days. After 15 days, the conditioned medium was collected in 225 mL BD Falcon polypropylene conical tubes (BD 352075—Blue Top) and centrifuged at 2,000 rpm for 20 minutes at 4° C. to remove cells and debris (care was taken not to disturb the pellet). The conditioned medium was run through a 0.45 μm membrane filter. The conditioned medium was concentrated using centrifugal filter. A 3 KDa Centricon Plus-70 Centrifugal Filter was pre-rinsed with 10-25 mL of molecular grade water and was centrifuged at 3220 g for five minutes at 18° C. Once the filter was rinsed, all remaining water was carefully removed without touching the filter. 15 mL of the conditioned medium was added to the filter and was centrifuged at 3220 g for 45 minutes at 18° C. After the initial spin, the remaining medium was mixed by pipetting and then spun again until the desired concentration was reached. The final sample was then run through a 0.22 m syringe filter. 25 μL of the concentrated conditioned medium was diluted in 975 μL of PBS for particle count using the Nanosight.

Another 100 μL of the concentrated conditioned medium was used to measure protein concentration. Protein was quantified using the DC protein Assay. In some cases, historical data was used to calculate the concentration of protein in the ultra-filtration by centrifugation (UFC) sample. The concentrated conditioned medium was used immediately or was stored at −80° C.

Example 3: Exosome Precipitation with 25% Polyethylene Glycol (PEG)

The appropriate volume of 25% PEG was added to the filtered concentrated conditioned medium. The samples were incubated at 4° C. for 12-16 hours on an orbital shaker. Once incubation was complete, the samples were centrifuged at 1500 g for 30 minutes at 4° C. The supernatant was carefully removed without disrupting the pellet. The pellet was resuspended in the desired volume of serum-free medium and sampled for particle count.

Example 4: CDC-EVs: 10 KDa & 1000 KDa Method; MSC-EVs; Newt-EVs

A) 10 KDa & 1000 KDa Method

CDC-EV (10 KDa or 1000 KDa) drug substance is obtained after filtering CDC conditioned medium (CM) containing EVs through a 10 KDa or 1000 KDa pore size filter. The final product, composed of secreted EVs and concentrated CM, is formulated in PlasmaLyte A and stored frozen.

B) MSC-EVs

Extracellular vesicles originating from human bone marrow mesenchymal stem cells (MSC-EVs) are obtained after filtering MSC CM containing EVs through a 10 KDa pore size filter following a similar process as for CDC-EV production. MSC-EVs are a non-cellular, filter sterilized product obtained from human MSCs cultured under defined, serum-free conditions. The final product, composed of secreted EVs and concentrated CM, is formulated in PlasmaLyte A and stored frozen. The frozen final product is "ready to use" for direct subconjunctival injection after thawing.

C) Newt-EVs

Extracellular vesicles originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Example 5: Test and Control Articles

The test article is a non-cellular, filter sterilized product obtained from human CDCs cultured under defined, serum-free conditions, prepared as exemplified in Examples 1-4. The general characteristics of the test article are summarized in Table 2.

TABLE 2

| Characteristics | Description |
| --- | --- |
| Test article | CDC-EVs |
| Control article | PlasmaLyte A solution (Baxter) |
| Pharmaceutical form | CDC-EV suspension in PlasmaLyte for injection |

TABLE 2-continued

| Characteristics | Description |
| --- | --- |
| Dosage/Strength | Low dose: $1.00 \times 10^9$ particles/200 µL (1x/week); High dose: $1.00 \times 10^{10}$ particles/200 µL (1x/week) for Days 21, 28 and 35, and switched to $3.33 \times 10^9$ particles/200 µL (2x/week) for Days 43, 47 and 50 |
| Fill/Vial Size | 0.4 mL per 2 mL vial |
| Product Container | CellSeal ® closed-system vial with needleless luer fittings |
| Storage Conditions | Frozen at $-80°$ C. |

Individual exosome vials were thawed at 4° C. or on ice. After each aliquot was completely thawed it was mixed gently (~6-8 times, avoiding excessive bubbling/foaming) using a micropipette, or an insulin/Hamilton type syringe with an integrated needle, prior to first administration.

The test and control articles were thawed for dosing overnight or on the day of dosing, and kept on wet ice throughout the dosing procedures.

Example 6: Systemic GVHD Animal Model; Study Design; Assessment of GVHD

Recipient BALB/c mice (n=45, male, 6-8 weeks of age) and donor C57BL/6 (n=30, male 6-10 weeks) were obtained from Charles River Laboratories (Wilmington, Mass.). Animals were acclimatized prior to study commencement. During this period, the animals were observed daily in order to reject any that presented in poor condition.

The study was performed in animal rooms provided with HEPA filtered air at a temperature of 70±5° F. and 50%±20% relative humidity. Animals were housed in groups of 15 per cage. Animal rooms were set to maintain a minimum of 12-15 air changes per hour. The room was on an automatic timer for a light/dark cycle of 12 hours on and 12 hours off with no twilight. Sterile Alpha-dri® bedding was used. Animals were fed with LabDiet 5053 sterile rodent diet and water was provided ad libitum.

Figure 5:
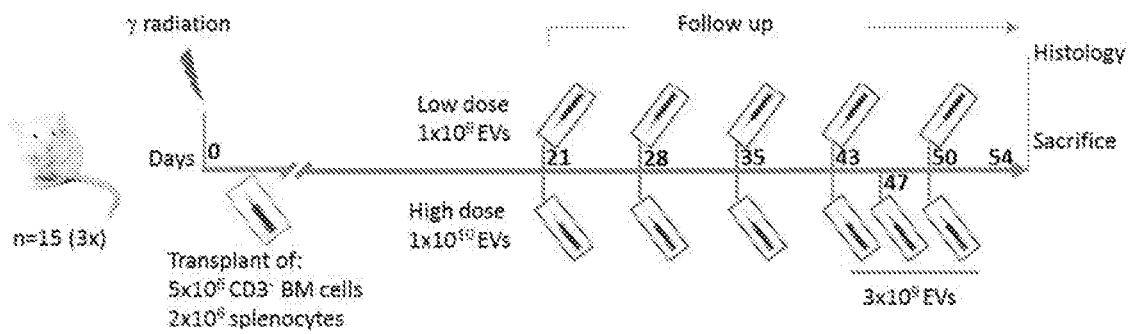
FIG. 5 schematically illustrates the study design for evaluating the efficacy of extracellular vesicles to treat systemic GVHD.

FIGS. 1 and 5 illustrate how the animal model of systemic GVHD was generated, based on, e.g., Schroeder and DiPersio, "Mouse Models of Graft-Versus-Host Disease: Advances and Limitations," *Disease Models & Mechanisms*, 4:318-333 (2011); van Leeuwen et al., "A Two-Phase Pathogenesis of Graft-Versus-Host Disease in Mice," *Bone Marrow Transplantation*, 29:151-158 (2002), with a few modifications. On Day -1, BALB/c mice were subjected to a single acute dose of 8 Gy of total body irradiation (TBI). On Day 0, the BALB/c recipients were given an intravenous injection, using a syringe with 30 gauge needle into the tail vein, of a combination of $2 \times 10^6$ splenocytes and T-cell depleted (CD3$^-$) bone marrow cells $5 \times 10^6$ in sterile 1×PBS. Bone marrow (BM) and splenic cells (SC) were obtained from donor male C57BL/6 mice. The bone marrow cells were isolated using standard flushing practices and T-cell depleted using the cell surface T-cell antigen CD3, with a CD3-biotin kit from Miltenyi Biotec (130-093-021). Recipient animals were randomized into 3 groups of 15 animals each.

Following TBI on Day -1 up to Day 8, all animals were given supplemental high calorie highly palatable food in a dish on the bottom of the cage. Following transfer on Day 0, and then again as needed, all animals were given 1 mL/animal/day of supplemental fluids (warmed ringers solution) via subcutaneous injection. An additional 1 mL fluid may have been given in the afternoon on an as needed basis. Any animal exceeding -15% body weight loss was given highly palatable soft food and 1 mL supplemental fluids (warmed ringers solution) via subcutaneous injection.

Animals were dosed with the vehicle or the test article as detailed in Table 3 and as illustrated in FIG. 5.

TABLE 3

| Group | n | TBI (Day -1) | Cell transfer (Day 0) | Treatment | Schedule | Sacrifice | Collections |
| --- | --- | --- | --- | --- | --- | --- | --- |
| 1 | 15 | 8 Gy | $5 \times 10^6$ BM and $2 \times 10^6$ SC | PlasmaLyte | 21, 28, 35, 43 and 50 (1x/week) | Day 54 | Plasma, liver, lung, eye, femur, colon |
| 2 | 15 | 8 Gy | $5 \times 10^6$ BM and $2 \times 10^6$ SC | Low dose: $1.00 \times 10^9$ CDC-EVs | 21, 28, 35, 43 and 50 (1x/week) | Day 54 | Plasma, liver, lung, eye, femur, colon |
| 3 | 15 | 8 Gy | $5 \times 10^6$ BM and $2 \times 10^6$ SC | High dose: $1.00 \times 10^{10}$ or $3.33 \times 10^9$ CDC-EVs | $1.00 \times 10^{10}$ at Days 21, 28 and 35 (1x/week), and $3.33 \times 10^9$ at Days 43, 47 and 50 (2x/week) | Day 54 | Plasma, liver, lung, eye, femur, colon |

Every day for the study period, each animal was weighed and its survival was recorded in order to assess possible differences among treatment groups and as an indication for GVHD severity and/or possible toxicity resulting from the treatments. Any animal losing >30% of their starting weight was euthanized.

Figure 2A:
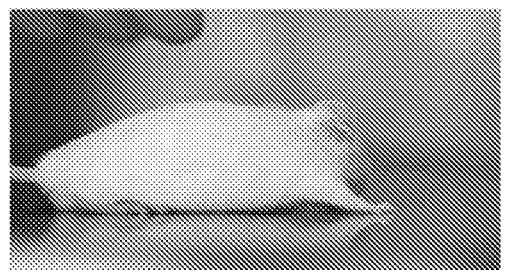
FIG. 2A is a photograph showing an example of Grade 0 for the posture criterion of the GVHD score.
Figure 2B:
FIG. 2B is a photograph showing an example of Grade 1 for the posture criterion of the GVHD score.
Figure 2C:
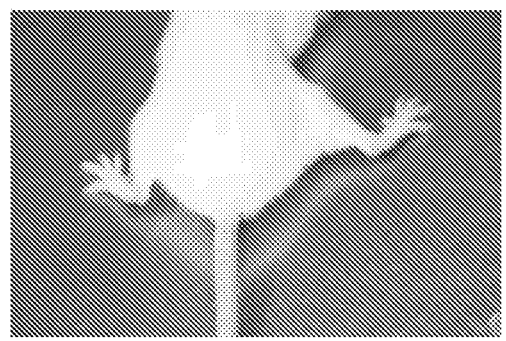
FIG. 2C is a photograph showing an example of Grade 2 for the posture criterion of the GVHD score.
Figure 3A:
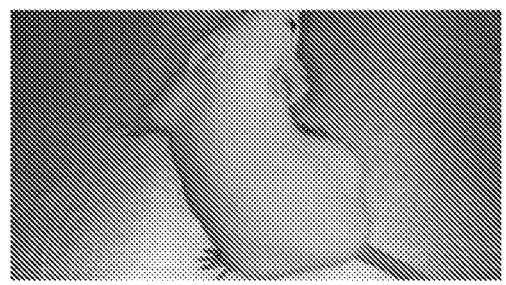
FIG. 3A is a photograph showing an example of Grade 0 for the fur texture criterion of the GVHD score.
Figure 3B:
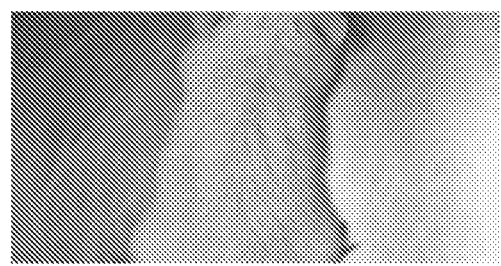
FIG. 3B is a photograph showing an example of Grade 1 for the fur texture criterion of the GVHD score.
Figure 3C:
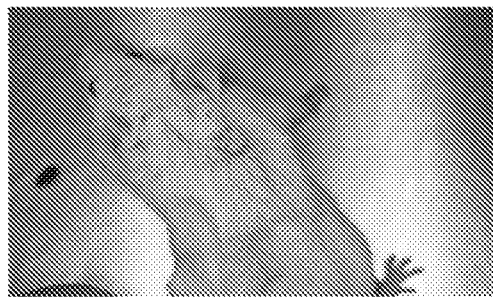
FIG. 3C is a photograph showing an example of Grade 2 for the fur texture criterion of the GVHD score.
Figure 4A:
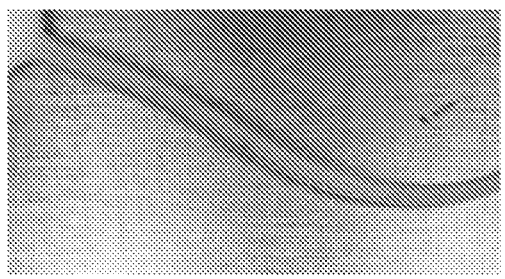
FIG. 4A is a photograph showing an example of Grade 0 for the skin integrity criterion of the GVHD score.
Figure 4B:
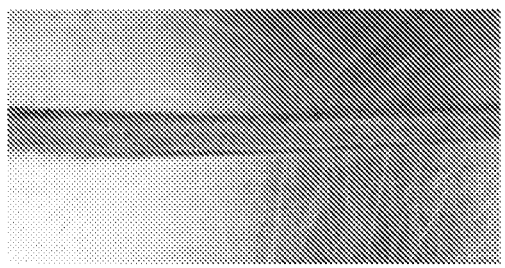
FIG. 4B is a photograph showing an example of Grade 1 for the skin integrity criterion of the GVHD score.
Figure 4C:
FIG. 4C is a photograph showing an example of Grade 2 for the skin integrity criterion of the GVHD score.

A clinical score for GVHD was obtained twice weekly for the entire study duration as assessed by a standard scoring system as detailed in Table 4, wherein the overall GVHD score was based on 5 criteria: percentage of weight change, posture (hunching) as exemplified in FIGS. 2A-C, activity, fur texture as exemplified in FIGS. 3A-C, and skin integrity as exemplified in FIGS. 4A-C, with the maximum index=10.

TABLE 4

| Criteria | Grade 0 | Grade 1 | Grade 2 |
| --- | --- | --- | --- |
| Weight loss | <10% | >10%, <25% | >25% |
| Posture | Normal | Hunching noted only at rest | Severe gait, impaired movement |
| Activity | Normal | Mild to moderately decreased | Stationary until stimulated |

TABLE 4-continued

| Criteria | Grade 0 | Grade 1 | Grade 2 |
|---|---|---|---|
| Fur texture | Normal | Mild to moderate ruffling | Severe ruffling and/or poor grooming |
| Skin integrity | Normal | Scaling of paws and/or tail | Obvious areas of denuded skin |

All animals were followed for at least 54 days. At the end of the study, all surviving animals were sacrificed by an overdose of $CO_2$ and organs detailed in Table 4 were collected. Upon sacrifice, blood was collected by retro-orbital bleed into $K_2EDTA$ tubes. The blood was centrifuged and the plasma collected, flash frozen, and stored at −80° C. for further downstream analyses. Upon sacrifice, the liver was excised and the caudate lobe placed directly in formalin for 24 hours prior to transfer to 70% ethanol for long term storage. Upon sacrifice, the lungs and heart were removed en bloc, and the lungs were perfused with formalin through the heart right ventricle. The left (non-lobular) lung was removed and placed directly in formalin for 24 hours prior to transfer to 70% ethanol for long term storage.

Example 7: Outcome Evaluation & In-Life Monitoring

A) Statistical Analyses

Parametric data (weight change, engraftment) were evaluated using one-way ANOVA with Holm-Šidák's multiple comparison test to compare all groups to the vehicle control group. Non-parametric data (GVHD scores) were analyzed with Kruskal-Wallis with Dunn's post-hoc test. All statistical analyses were performed using GraphPad Prism 6.01 Software (La Jolla, Calif.). Statistical significance was achieved when $p<0.05$.

B) GVHD Score

Figure 7A:
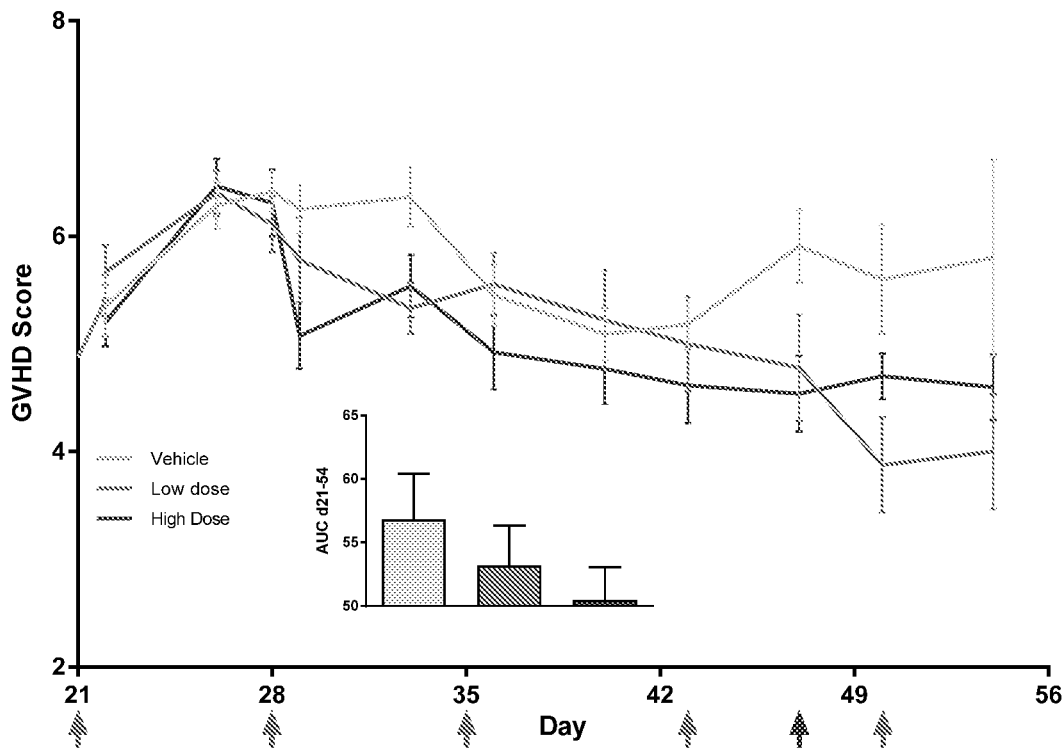
FIG. 7A graphically shows the effects of intravenous administration of extracellular vesicles on the overall GVHD score.

As assessed using the multi-parameter GVHD scoring systems shown in Table 4 and as shown in FIG. 7A, intravenous injection of splenocytes and bone marrow cells induced GVHD in all animals. As shown in FIG. 7A, decreases in the overall GVHD score were observed in both groups dosed with CDC-EVs, and individual GVHD parameters (posture, activity, fur texture, skin integrity) are summarized in FIGS. 8A-D.

When an animal was forced to be euthanized because it had lost too much weight (>30% per IACUC protocol), the last observation was carried forward into subsequent data points to include the data for the dead animal.

Figure 7B:
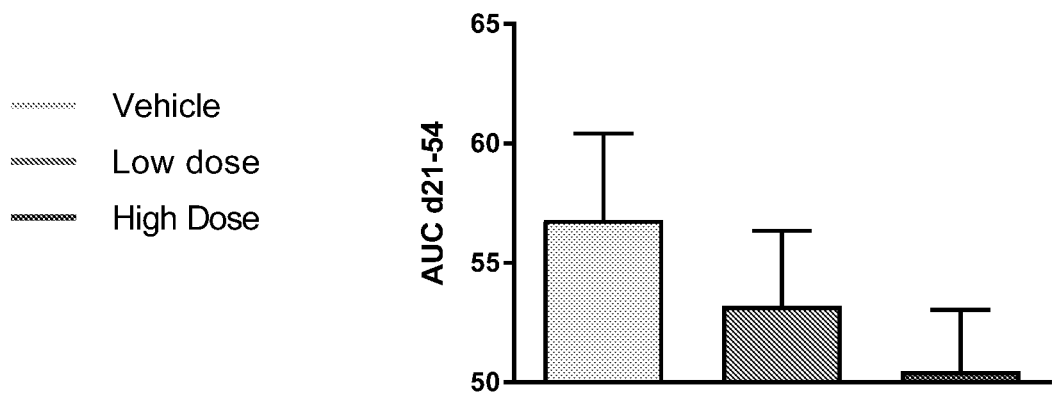
FIG. 7B shows the same data of FIG. 7A as AUC to enable effective comparison of groups by statistical test.

Referring to FIG. 7B, the AUC was calculated to enable effective comparison of the groups by statistical test.

C) Body Weight Change

Figure 6A:
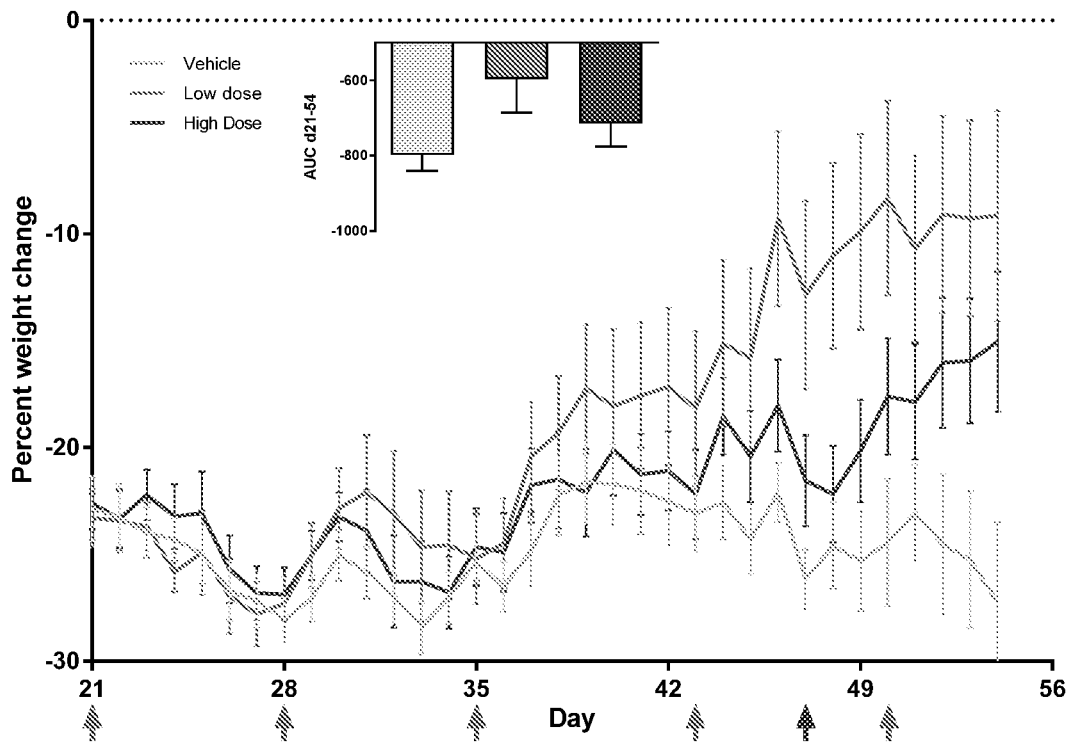
FIG. 6A graphically shows the effects of intravenous administration of extracellular vesicles on the weight of the mouse model of systemic GVHD.

As shown in FIG. 6A, intravenous injection of splenocytes and bone marrow cells induced weight loss in all animals, and variable gains and losses were observed through the conclusion of the study. Following the initiation of dosing on Day 21, all animals continued to exhibit weight loss, peaking at around Day 33 followed by a partial recovery up until around Day 40. Animals dosed with either low dose or high dose of CDC-EVs continued to experience a general gain in weight up until the conclusion of the study on Day 54, whereas animals treated with the vehicle alone continued to lose weight. Indeed, the vehicle-treated animals had lost so much weight toward the end of the study that many of them were expected to die.

When an animal was forced to be euthanized because it had lost too much weight (>30% per IACUC protocol), the last observation was carried forward into subsequent data points to include the data for the dead animal.

Figure 6B:
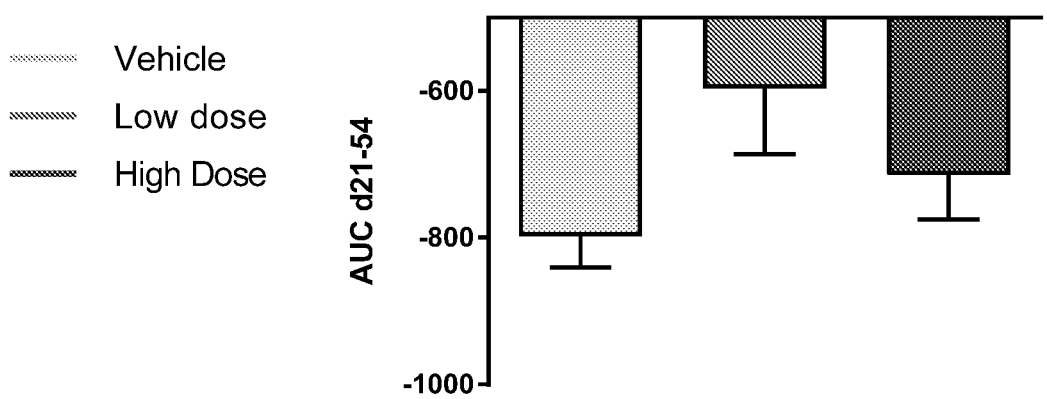
FIG. 6B shows the same data of FIG. 6A as AUC to enable effective comparison of groups by statistical test.

Referring to FIG. 6B, the AUC was calculated to enable effective comparison of the groups by statistical test.

D) Survival

Figure 9:
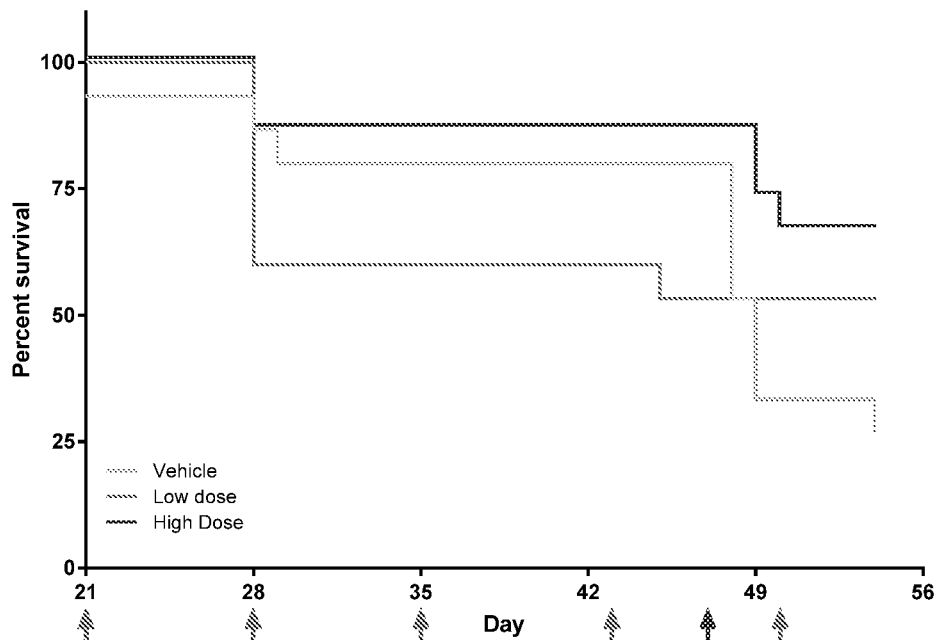
FIG. 9 graphically shows the effects of intravenous administration of extracellular vesicles on the survival of the mouse model of systemic GVHD.

As shown in FIG. 9, survival was tracked for all animals for the duration of the study and the percent survival was plotted, wherein treatment with both low dose and high dose CDC-EVs appeared to have beneficial effects on survival.

E) Bloody Stool & Diarrhea Incidence

Figure 10A:
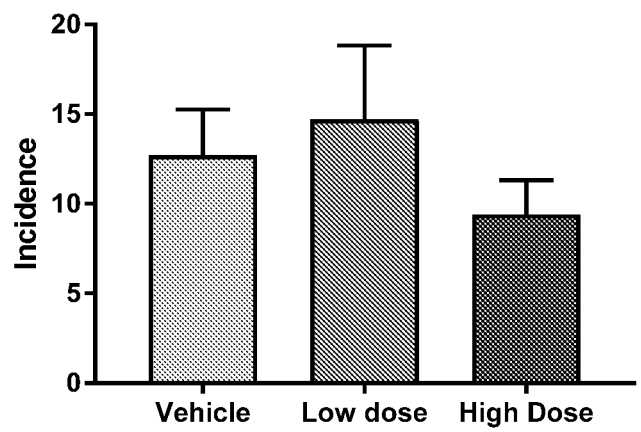
FIGS. 10A-B graphically show the effects of intravenous administration of extracellular vesicles on the diarrhea incidence of the mouse model of systemic GVHD.
Figure 10B:
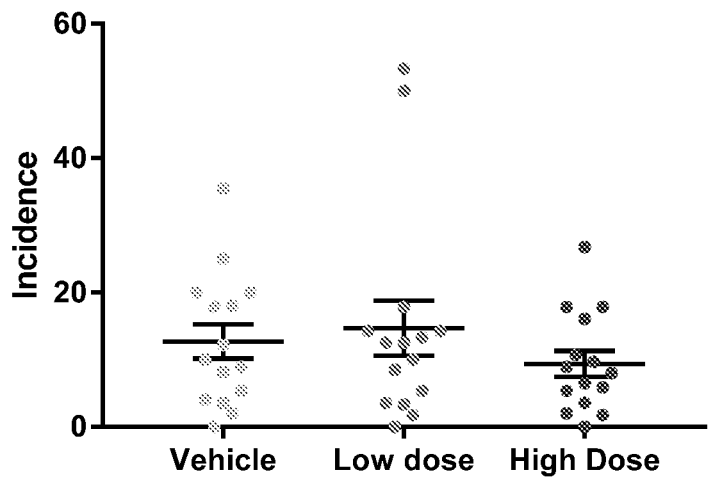

The incidence of bloody stool and diarrhea was tracked for the entire duration of the study. There was no incidence of bloody stool at any point during the study (data not shown). As shown in FIGS. 10A-B, treatment with high dose CDC-EVs appeared to decrease the incidence of diarrhea, although no dramatic effect on diarrhea incidence was observed as a result of treatment with CDC-EVs.

F) Eye Inflammation

Figure 11A:
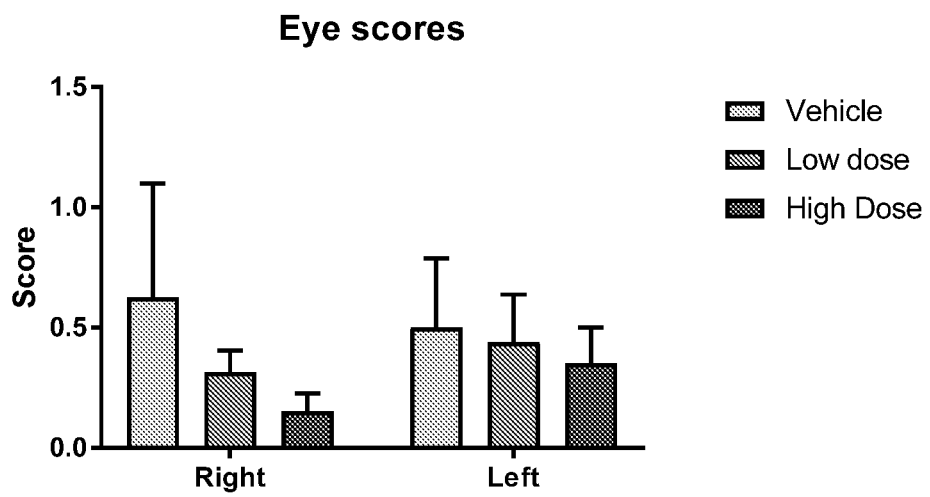
FIGS. 11A-C graphically show the effects of intravenous administration of extracellular vesicles on the eye inflammation of the mouse model of systemic GVHD.
Figure 11B:
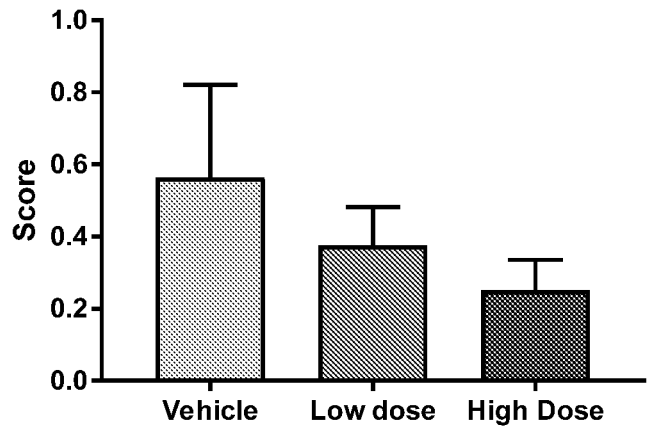
Figure 11C:
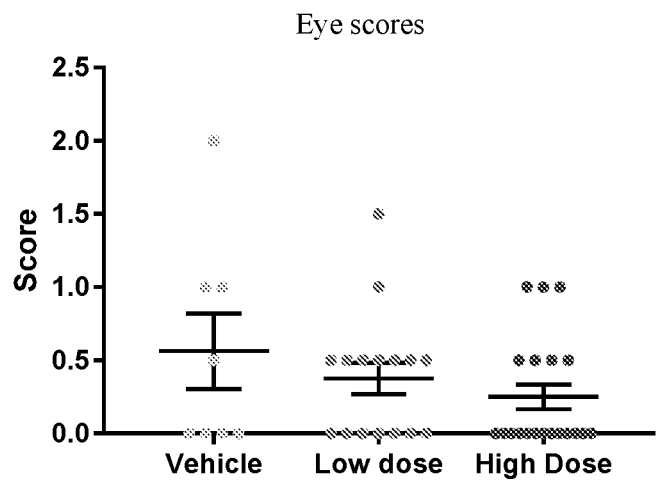

Immediately prior to sacrifice at Day 54, eye inflammation was assessed and scored, wherein a drop of 1% sodium fluorescein was applied to each eye, then the eye was rinsed off with saline, and viewed the fluorescence of the cornea with cobalt blue light under magnification. A masked/blinded observer assigned a score of 0 through 4 to each eye of each animal based on the degree of corneal fluorescein staining seen in the eye as follows: 0=no staining; 0.5=trace punctate staining; 1=punctate staining; 2=up to 25% staining of the corneal surface area; 3=up to 50% staining of the corneal surface area; 4=>50% corneal surface staining. The scores for each eye were averaged to achieve an "eye score" for each group. FIGS. 11A-C show that while there was a trend toward lower eye score (therefore less corneal staining, a sign that there is reduced eye inflammation) in the CDC-EV-treated groups, with the high dose-treated animals performing even better.

Example 8: Histopathologic Examination 14 mouse colon samples and 14 mouse eyes from the animals of Groups 1-3 as described in Table 3 were processed routinely for histopathologic examination. One slide per block was sectioned and stained with hematoxylin and eosin (H & E) or microscopic analysis of tissue structure and inflammatory infiltrate. Glass slides were evaluated using light microscopy by a board-certified veterinary pathologist; colons were qualitatively evaluated and scored for inflammation, edema, mucosal erosion, and goblet cell depletion according to the histopathologic criteria listed in Tables 5-8. Each of the longitudinal sections on a given slide was scored. The mean score was calculated and reported for each parameter. Additionally, the mean sum score was calculated as the sum of inflammation, edema, mucosal necrosis, and goblet cell depletion.

TABLE 5

| Inflammation Score | Description |
|---|---|
| 0 | None present |
| 1 | Minimal change: Focal aggregate of a few cells of minimal diffuse inflammation |
| 2 | Mild change: Larger focal aggregates, multifocal small aggregates, or diffuse mild inflammation |

TABLE 5-continued

| Inflammation Score | Description |
|---|---|
| 3 | Moderate change: Multifocal aggregates sometimes coalescing with one another or moderate diffuse change |
| 4 | Severe change: Marked diffuse inflammation |

TABLE 6

| Edema Score | Description |
|---|---|
| 0 | None present |
| 1 | Minimal change: Focal edema or minimal diffuse edema |
| 2 | Mild change: Larger focal areas of edema or diffuse mild edema |
| 3 | Moderate change: Multifocal areas of edema coalescing with one another or moderate diffuse edema |
| 4 | Severe change: Marked diffuse edema |

TABLE 7

| Mucosal Necrosis/ Epithelial Damage Score | Description |
|---|---|
| 0 | None present |
| 1 | Minimal change: Focal epithelial necrosis |
| 2 | Mild change: Larger focal areas of necrosis or multifocal areas of necrosis |
| 3 | Moderate change: Multifocal necrosis coalescing into larger areas |
| 4 | Severe change: Areas of erosion through the mucosa to the submucosa |

TABLE 8

| Goblet Cell Depletion Score | Description |
|---|---|
| 0 | None present |
| 1 | Minimal change: Focal goblet cell loss in one or a few colonic glands |
| 2 | Mild change: Larger focal areas of goblet cell loss, or multifocal goblet cell loss in several glands |
| 3 | Moderate change: Multifocal to regionally extensive goblet cell loss |
| 4 | Severe change: Marked diffuse goblet cell loss |

Scores for each feature were summed to obtain a sum colitis score (range 0-16). Colonic histologic lesions not addressed in this grading scheme and lesions in eye sections were scored semi-quantitatively 0-5, where 0=not present, 1=minimal, 2=mild, 3=moderate, 4=marked, 5=severe. See, e.g., Crissman et al., "Best Practices Guideline: Toxicologic Pathology," Toxicol Pathol, 32: 126-31 (2004).

A) Colon

Expected histologic lesions of GVHD colitis in mice included primarily mononuclear inflammation in the colonic mucosa; expansion of the submucosa and lymphatic vessels by edema; epithelial damage or mucosal necrosis, with or without erosion and infiltration of neutrophils; and depletion of goblet cells. See, e.g., Eigenbrodt et al., "Histologic Similarity of Murine Colonic Graft-versus-host Disease (GVHD) to Human Colonic GVHD and Inflammatory Bowel Disease," Am J Pathol, 137: 1065-76 (1990). Additional expected lesions included lymphocytic satellitosis, the infiltration of lymphocytes into the colonic gland with epithelial cell apoptosis; epithelial hyperplasia, characterized by gland elongation, basophilia and increased mitotic figures; and mesenteric adipose necrosis with subacute inflammation, the infiltration of neutrophils, macrophages and fewer lymphocytes and plasma cells into the mesentery adjacent the colon.

Figure 12:
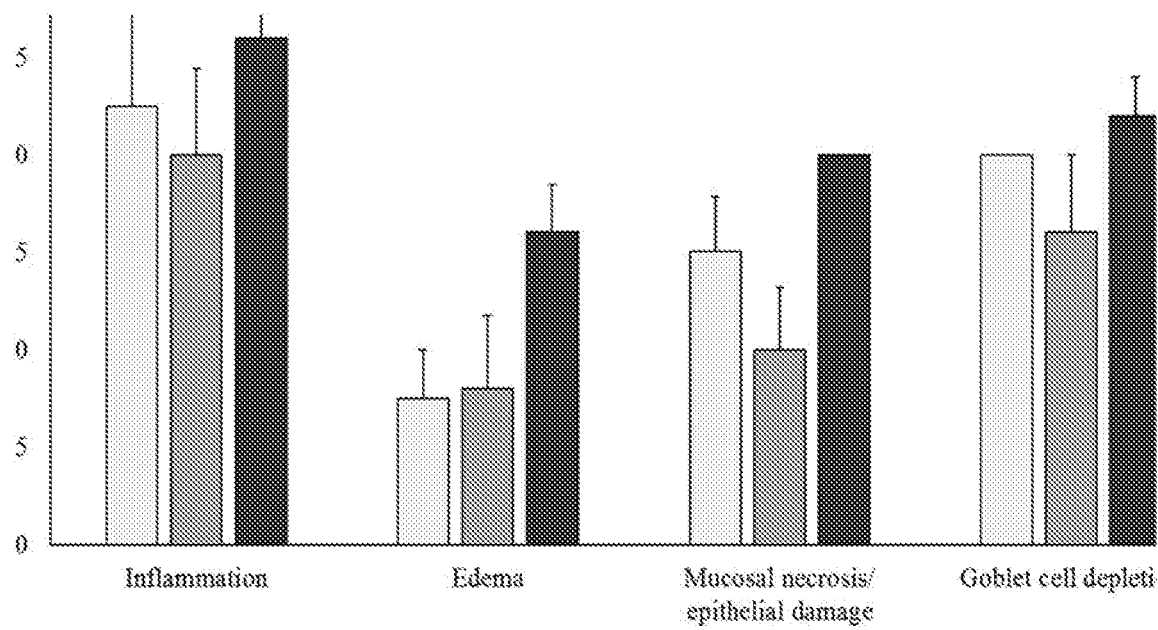
FIG. 12 graphically shows the effects of intravenous administration of extracellular vesicles on the colitis scores of the mouse model of systemic GVHD.
Figure 13:
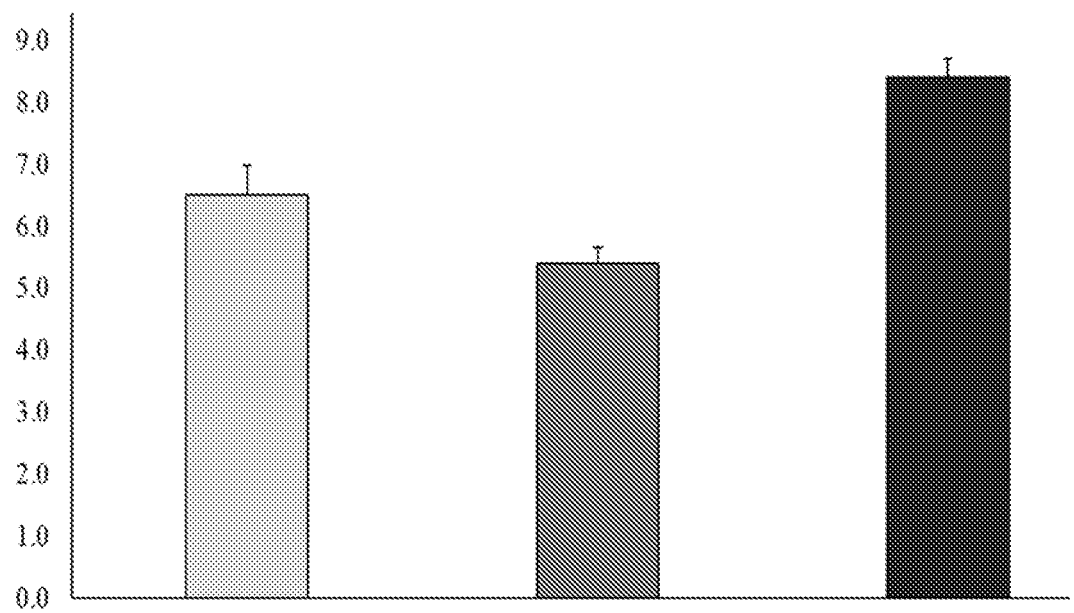
FIG. 13 graphically shows the same data as in FIG. 12 as sum colitis scores.
Figure 14:
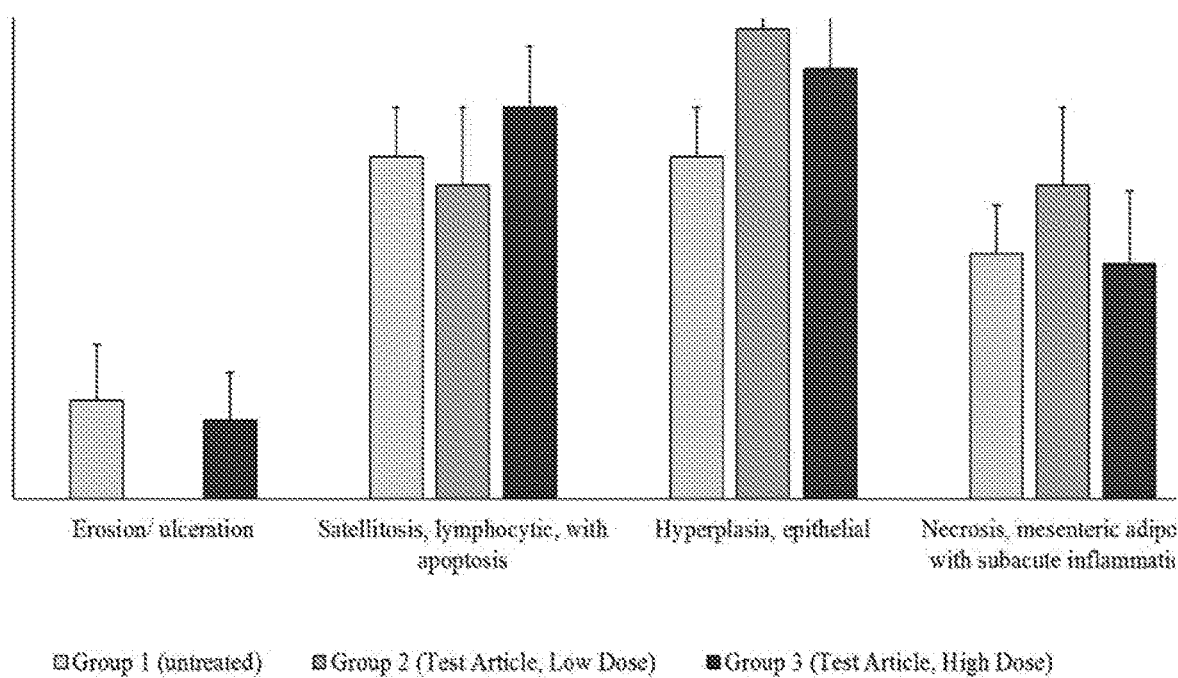
FIG. 14 graphically shows the effects of intravenous administration of extracellular vesicles on the colon histopathology severity scores of the mouse model of systemic GVHD.

As shown in FIGS. 12-13, decreases in mucosal necrosis and goblet cell depletion scores in the test article-low dose group (Group 2) translated into a reduction in sum score compared to the untreated group (Group 1).

B) Eye

Expected histologic lesions in eyes from mice with GVHD included lymphocytic satellitosis, characterized by infiltration of low numbers of lymphocytes into the corneal epithelium, with concurrent epithelial cell vacuolization and/or apoptosis; corneal epithelial necrosis with progression to ulceration was present in one sample. See, e.g., Perez et al., "Limbus Damage in Ocular Graft-versus-Host-Disease," Biol Blood Marrow Transplant, 17: 270-273 (2011). Corneal subacute inflammation was characterized by infiltration of neutrophils, lymphocytes or histiocytes into the corneal stroma and/or epithelium, accompanied by stromal edema or occasional foci of stromal necrosis. Neovascularization was characterized by ingrowth of blood vessels into the corneal stroma. Subacute inflammation was also observed in the limbus, conjunctiva (when present) and the anterior uveal tract, including the iris or anterior chamber. Mineralization was visible in the corneal stroma or in the immediate sub-basilar zone of the corneal epithelium (sub-epithelial). Lens fiber degeneration (cataract formation), characterized by posterior migration and disorganization of the lens epithelium and bladder cell formation, was observed as well.

Figure 15:
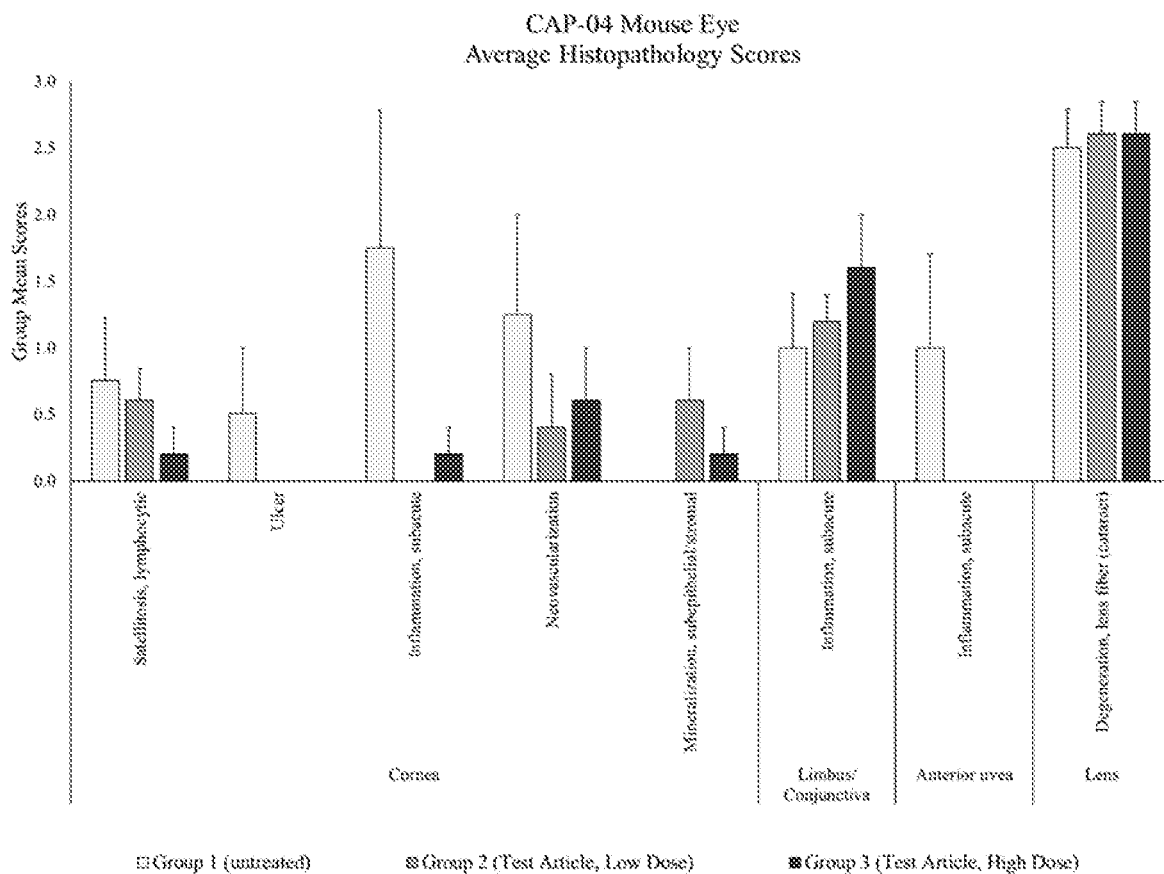
FIG. 15 graphically shows the effects of intravenous administration of extracellular vesicles on the eye average histopathology scores of the mouse model of systemic GVHD.

As shown in FIG. 15, lymphocytic satellitosis, corneal and anterior uveal subacute inflammation and neovascularization scores were most severe in Group 1 (untreated); with lower scores or complete absence of these lesions in the test article-treated animals (Groups 2 and 3).

Example 9: CDC-Derived Extracellular Vesicles (CDC-EVs) Interaction with T Cells The purpose of this study was to determine the immunological activity of CDC-EVs linked to T cells regulation.

Characterization of CDC-EVs & Immune Phenotype

Figure 16:
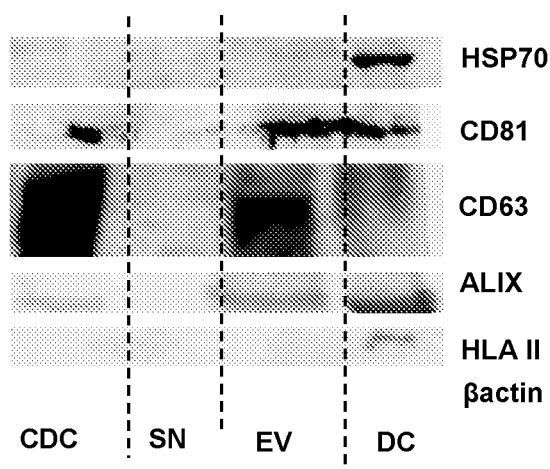
FIG. 16 is a western blot showing CDC-EVs' contents of recognized exosomes markers.

For FIG. 16, the expression of exosome informative markers was analyzed by CDC-EVs using Western blotting. CDC-EVs (20 µl=10 µg) were lysed using RIPA buffer and loaded to 10% SDS-Page gels then transferred to nitrocellulose membrane. Membranes were blocked with 5% BSA then hybridized with specific antibodies against HSP70, CD81, CD63, ALIX, HLA II and 3-actin. CDCs and dendritic cells (DC) lysates as well as exosome-free supernatant (SN) were used as controls. CDC-EVs expressed expected exosome markers CD81, CD63 and ALIX while SN was completely negative.

CDC-EVs were next analyzed for the surface expression of immune relevant markers. CDC-EVs (30 µl=15 µg) have been coupled to 5 µl Latex beads (4 µm). CDC-EVs/beads were treated successively with 100 mM glycine and 2% BSA buffers in order to block any eventual non-specific binding of these EVs/beads with antibodies or with beads. After washing, EVs/beads were stained with specific antibodies against relevant immune molecules acquired on Canto II BD Facs and analyzed by FlowJo software. Beads incubated with the same amount of respective antibodies were used as a control.

Figure 17:
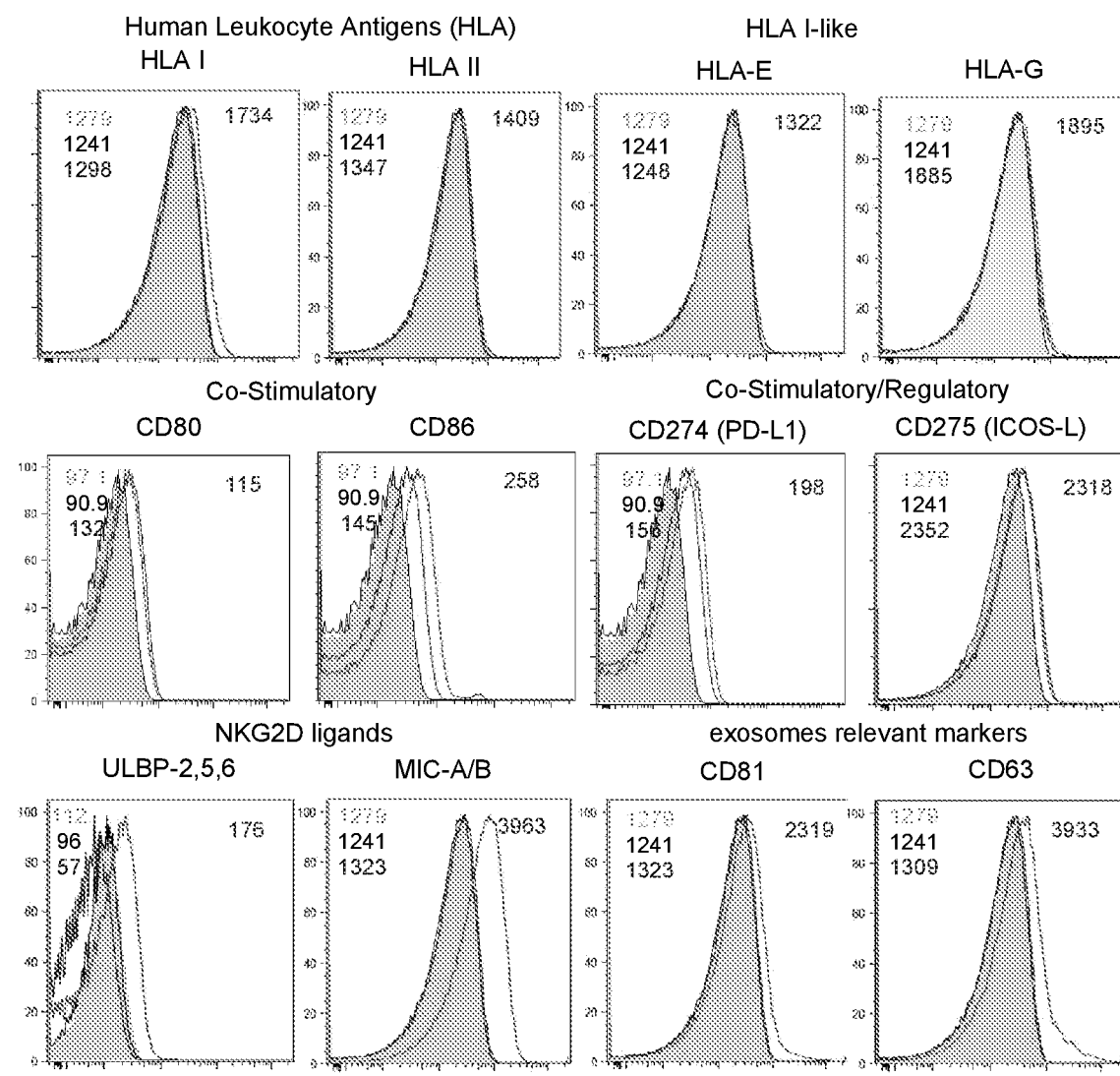
FIG. 17 graphically shows the expression of immune molecules involved in T and natural killer (NK) immune response on CDC-EVs.

Compared to beads-antibody control, CDC-EVs expressed HLA class I molecules and CD86, but were negative for HLA II and CD80 molecules. CDC-EVs seem to express the co-stimulatory PD-L1 molecule but not the ICOS-L. NK activating receptor ligands were remarkably expressed on the CDC-EVs. For FIG. 17, significant expression of both EVs markers CD81 and CD63 was detected.

Indirect T Cells Activation and Proliferation in Response to Allogeneic EVs

Monocytes were isolated from blood samples obtained from two different healthy donors. Isolated-monocytes were then stimulated for 6 days with a combination of GM-CSF (20 ng/ml) and IL4 (20 ng/ml) to allow their differentiation to DC. Differentiation of monocytes with GM-CSF+IL4 generates immature DC (iDC) marked by moderate expression of HLA II, CD80, and CD86 molecules, absence of CD16 (marker of monocytes/macrophages), and low expression of TLR-2. These monocyte-derived iDC were then incubated for an overnight with HLA-mismatched CDC-EVs.

iDC cultured with EVs displayed features of mature DC (mDC); they up-regulated their HLA II, CD80 and CD86 molecules, which is recognized as mDC properties, as shown in FIG. 28. Then $1\times10^4$ of iDCs or iDCs that were in contact with EVs (iDC-EVs) were co-cultured with autologous T cells ($1\times10^5$) in U-bottom 96 wells plates for another 6 days. Autologous T cells co-cultured with iDC or iDC-EVs where analyzed for their expression of CD69 and HLA-DR, and for their proliferation. Although the response of T cells from two different donors was variable, as a whole iDC-EV were more potent in activating and inducing the proliferation of T cells than iDCs alone, as shown in FIG. 29.

Compared to direct CDC-EV-induced T cells proliferation, the magnitude of indirect CDC-EV-induced T cells proliferation is fairly higher.

The capacity of CDC-EVs to stimulate T cells when presented by mature DC (mDC) was evaluated. Given that mDC have very low phagocytic activity and to insure appropriate uptake of EVs and based on previous experience of phagocytizing apoptotic bodies, the maturation of DC was induced by treating iDC and iDC-EVs for an overnight with IFNγ (500 IU/ml), which is a recognized inducer of DC maturation. Compared to iDC, these mDC showed higher expression of HLA II, CD80 and CD86, and higher expression of TLR-2, which are the know features of mDC. The presence of CDC-EVs during iDC maturation to mDC further up-regulated HLA II, CD86, CD80, and TLR-2 molecules, as shown in FIG. 30.

mDC or mDC-EVs were then co-cultured with autologous T cells ($1\times10^5$) fin U-bottom 96-wells plates or 6 days and their activation (expression of CD69 and HLA-DR) and proliferation was analyzed.

Again the responses from two donors, were variable but as a whole mDC-EVs were more potent in activating and inducing the proliferation of T cells than mDCs alone. Compared to iDC-EVs-induced response, mDC-EV-induced T cell activation and proliferation for the same donor was higher.

The ensemble of our results in regard of T cells activation and proliferation suggest that CDC-EVs can activate and induce the proliferation of T cells mainly through the indirect pathway without rolling out the direct pathway since we did observe weak direct activation.

In Vitro Uptake of CDC-EVs by T-Cells

Figure 18:
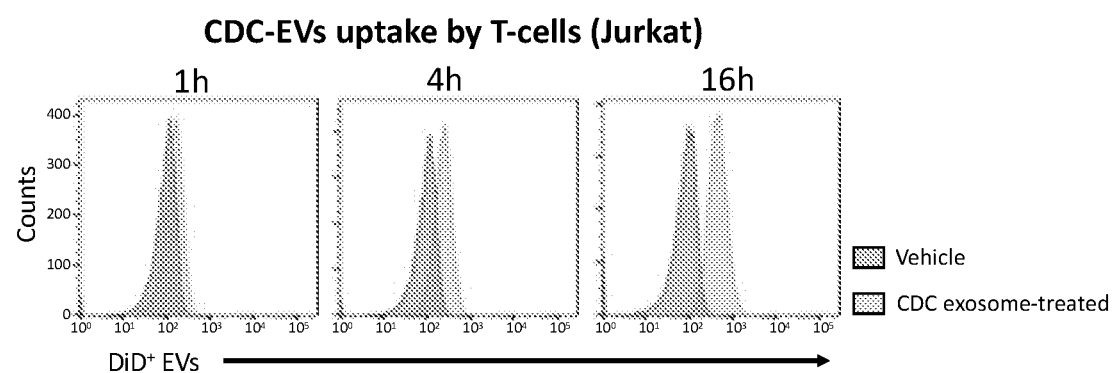
FIG. 18. Shows in vitro update of CDC-EVs in Jurkat T cells.

The ability of T cells for CDC-EVs uptake was evaluated in vitro. Human CDC-EVs were fluorescently labeled using the membrane dye DiD and were added to Jurkat T cells (Jurkat, Clone E6–; ATTC® TIN-152™). Uptake was measured by flow cytometry 1 hour, 4 hours, or overnight after addition of EVs. Jurkat T cells tested positive for DiD fluorescence at the different times tested, indicating that they uptake CDC-EVs (FIG. 18).

Immune-Modulation by CDC-EVs

Figure 19:
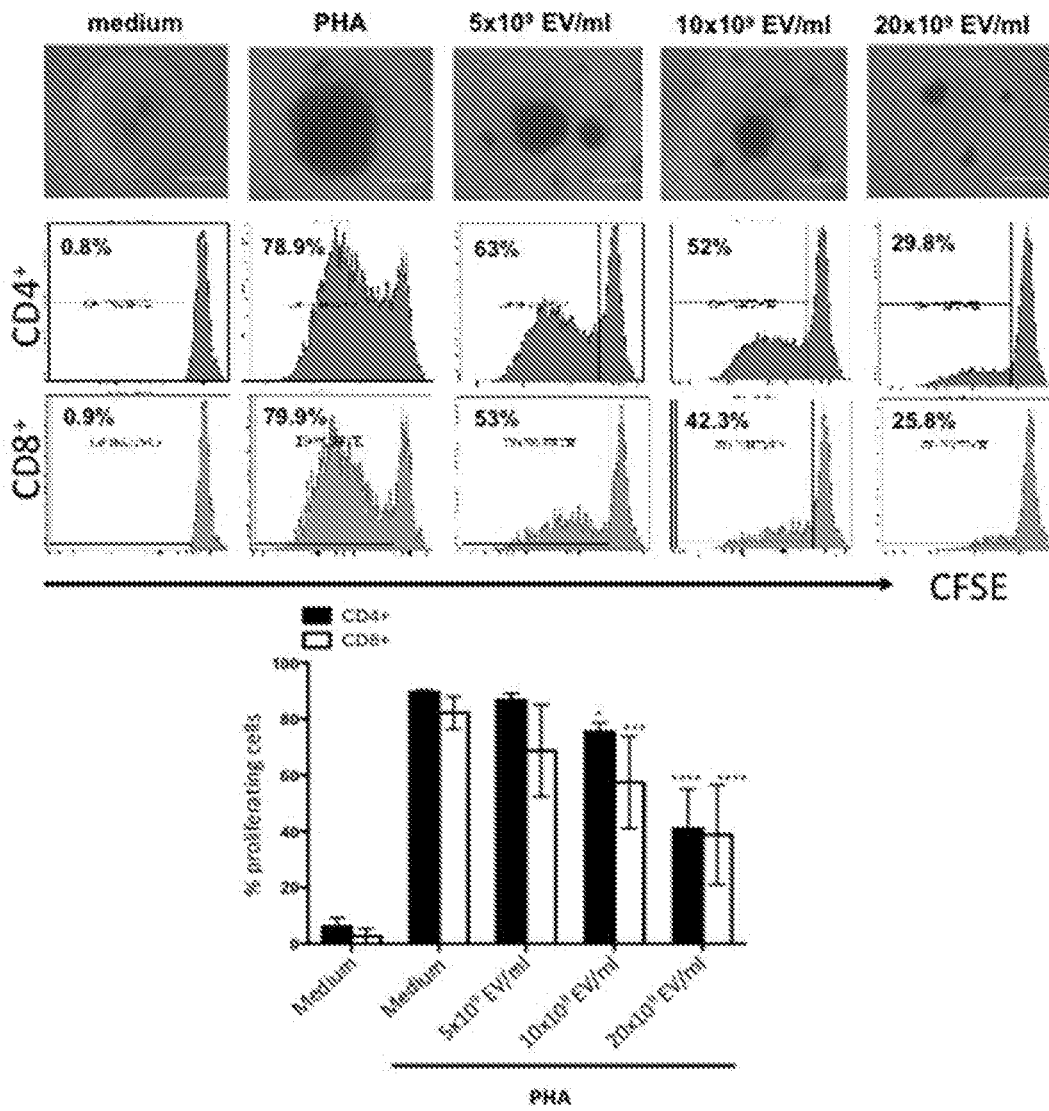
FIG. 19 shows the immune modulation of PHA-induced T cells proliferation by and CDC-EVs.

The capacity of CDC-EVs to modulate an ongoing immune response in an allogeneic setting was then investigated. To this end, HLA-mismatched unfractionated CFSE-labeled PBMC ($1\times10^5$) were stimulated with PHA (1 μg/ml) in the absence or presence of various doses of CDC-EVs as shown in FIG. 19 (upper panel) in U-bottom 96 well plates and allogeneic T cells proliferation was evaluated by monitoring CFSE. CDC-EVs were able to down regulate PHA-induced CD4$^+$ and CD8$^+$ T cell proliferation. CDC-EVs-induced down regulation of T cells proliferation was dose dependent, and at the highest used dose ($20\times10^9$ particles) CDC-EVs were more potent in down regulating ongoing response than their parental cells, as shown in FIG. 19.

Figure 20:
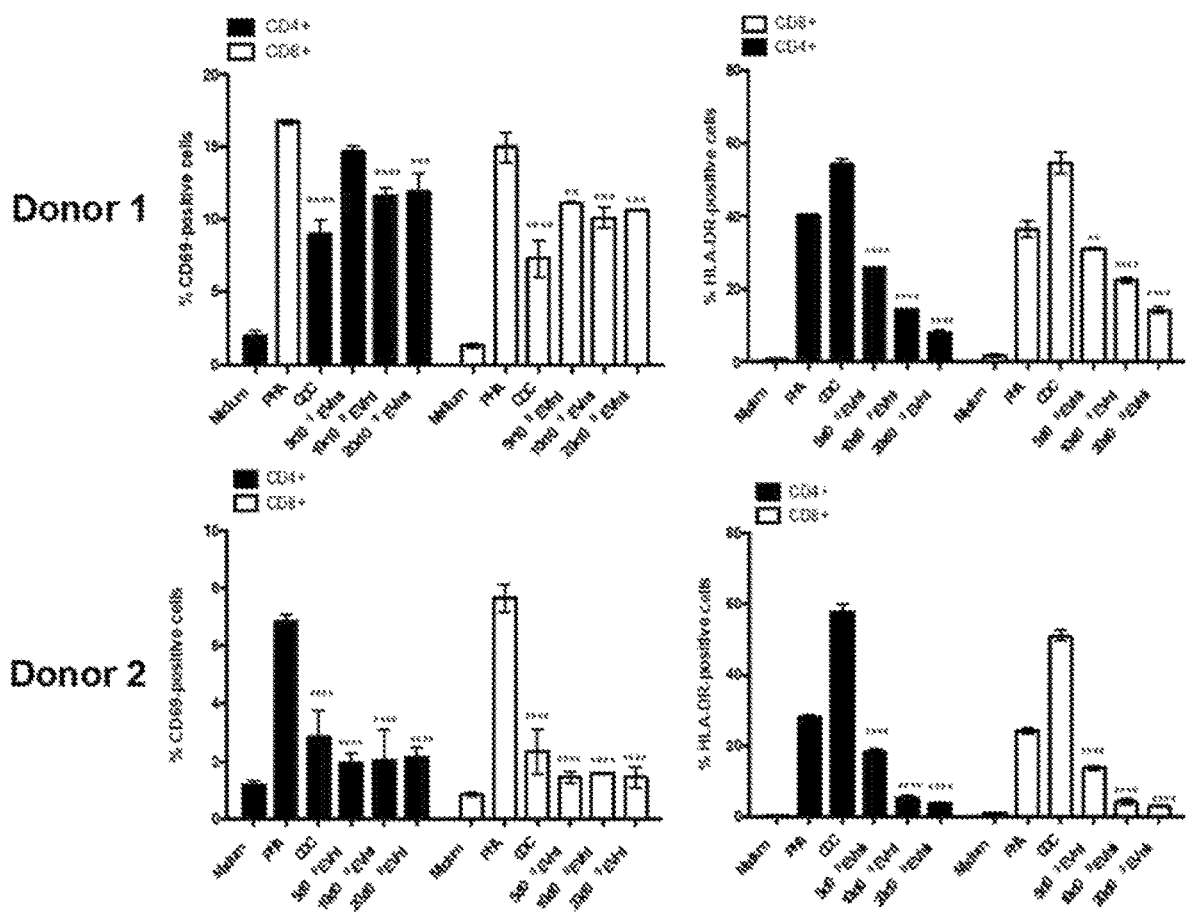
FIG. 20 graphically shows the down-regulation of PHA-induced CD69 and/or HLA-DR expression by CDCs and CDC-EVs.

CDC-EV-induced immune modulation is likely through direct effects since similar results were obtained when purified CD3$^+$ T cells were used instead of PBMC within the same experimental settings. Indeed, CDC-EVs were able to down regulate PHA-induced expression of CDC69 and/or HLA-DR on T cells obtained from 2 different donors, as shown in FIG. 20.

Figure 21:
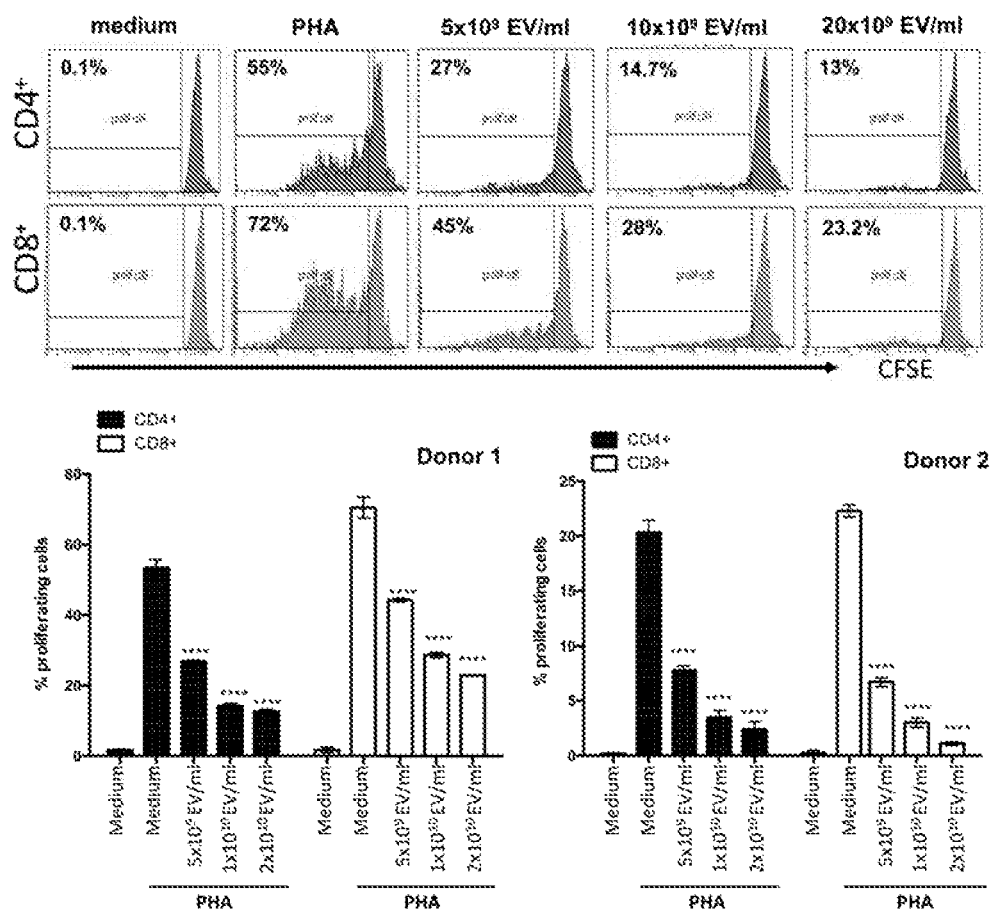
FIG. 21 graphically shows that CDC-EVs down regulate PHA-induced T cells proliferation.

For FIG. 21, down-modulation of T cells activation markers by CDC-EVs resulted in a pronounced down regulation of PHA-induced CD4$^+$ and CD8$^+$ T proliferation.

Figure 22:
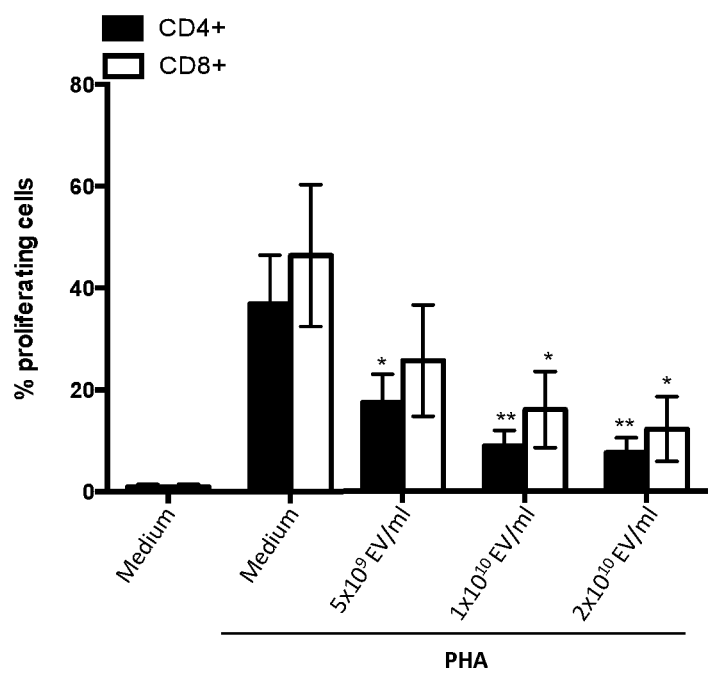
FIG. 22 graphically shows that immune modulation of PHA-induced $CD4^+$ and $CD8^+$ T cells proliferation by CDC-EVs.

For FIG. 22, despite inter-donor variability and within the limit of results obtained with two donors only, CDC-EVs are potent immune modulators.

These studies of capacity of CDC-EVs to induce immune-modulation demonstrated that they are potent immune-modulators.

The invention claimed is:

1. A method of treating systemic graft-versus-host disease (GVHD) in a subject in need thereof, the method comprising systemically administrating to the subject a therapeutically effective amount of extracellular vesicles, wherein said systemic GVHD is acute or chronic, wherein said extracellular vesicles express a natural killer cell (NK) activating receptor ligand, wherein said extracellular vesicles are obtained from cardiospheres, cardiosphere-derived cells (CDCs), or newt Al cell line, and wherein said NK activating receptor ligand is ULBP-2, 5, 6 or MIC-A/B.

2. The method according to claim 1, wherein said administration of a therapeutically effective amount of extracellular vesicles results in treatment of systemic GVHD with respect to at least one organ selected from the group consisting of the skin, mucosa, gastrointestinal tract, liver, and lungs.

3. The method according to claim 1, wherein said administration of a therapeutically effective amount of extracellular vesicles results in treatment of systemic GVHD with respect to at least two organs selected from the group consisting of the skin, mucosa, gastrointestinal tract, liver, and lungs.

4. The method according to claim 1, wherein said administration of a therapeutically effective amount of extracellular vesicles results in treatment of systemic GVHD with respect to at least one organ selected from the group consisting of the skin, mucosa, gastrointestinal tract, liver, lungs, joints and fascia, and genitalia.

5. The method according to claim 1, wherein said administration of a therapeutically effective amount of extracellular vesicles results in treatment of systemic GVHD with respect to at least two organs selected from the group consisting of the skin, mucosa, gastrointestinal tract, liver, lungs, joints and fascia, and genitalia.

6. The method according to claim 1, wherein said administration of a therapeutically effective amount of extracellular vesicles results in treatment of systemic GVHD with respect to at least one organ selected from the group consisting of the skin, mucosa, gastrointestinal tract, liver, lungs, joints and fascia, and genitalia, and the eyes.

7. The method according to claim 1, wherein said administration of a therapeutically effective amount of extracellular vesicles results in treatment of systemic GVHD with respect to the eyes.

8. The method according to claim 1, wherein a therapeutically effective amount of extracellular vesicles is administered one or more times after the subject has undergone hematopoietic stem cell transplant (HSCT).

9. The method according to claim 8, wherein a therapeutically effective amount of extracellular vesicles is administered 1, 2, 3, 4, 5, 6, 7, and/or 8 weeks after HSCT.

10. The method according to claim 1, wherein said systemic administration is via intra-vascular administration, intraventricular administration, intrathecal administration, subcutaneal administration, intradermal or intraperitoneal administration, wherein said intra-vascular administration is intravenous administration, intra-arterial administration, or intracoronary administration.

11. The method according to claim 1, wherein said extracellular vesicles are exosomes, microvesicles, membrane particles, membrane vesicles, exosome-like vesicles, ectosomes, ectosome-like vesicles, or exovesicles.

12. A method of treating systemic GVHD in a subject in need thereof, the method comprising systemically administrating to the subject a therapeutically effective amount of extracellular vesicles derived from CDCs, wherein said extracellular vesicles derived from CDCs express a natural killer cell (NK) activating receptor ligand, and wherein said NK activating receptor ligand is ULBP-2, 5, 6 or MIC-A/B.

13. The method according to claim 12, wherein said administration of a therapeutically effective amount of extracellular vesicles derived from CDCs results in treatment of systemic GVHD with respect to at least one organ selected from the group consisting of the skin, mucosa, gastrointestinal tract, liver, and lungs.

14. The method according to claim 12, wherein said administration of a therapeutically effective amount of extracellular vesicles derived from CDCs results in treatment of systemic GVHD with respect to at least two organs selected from the group consisting of the skin, mucosa, gastrointestinal tract, liver, and lungs.

15. The method according to claim 12, wherein said administration of a therapeutically effective amount of extracellular vesicles derived from CDCs results in treatment of systemic GVHD with respect to at least one organ selected from the group consisting of the skin, mucosa, gastrointestinal tract, liver, lungs, joints and fascia, and genitalia.

16. The method according to claim 12, wherein said administration of a therapeutically effective amount of extracellular vesicles derived from CDCs results in treatment of systemic GVHD with respect to at least two organs selected from the group consisting of the skin, mucosa, gastrointestinal tract, liver, lungs, joints and fascia, and genitalia.

17. The method according to claim 12, wherein said administration of a therapeutically effective amount of extracellular vesicles derived from CDCs results in treatment of systemic GVHD with respect to at least one organ selected from the group consisting of the skin, mucosa, gastrointestinal tract, liver, lungs, joints and fascia, and genitalia, and the eyes.

18. The method according to claim 12, wherein said administration of a therapeutically effective amount of extracellular vesicles derived from CDCs results in treatment of systemic GVHD with respect to the eyes.

* * * * *